United States Patent
Techentin et al.

(10) Patent No.: US 12,076,120 B2
(45) Date of Patent: Sep. 3, 2024

(54) SYSTEMS, METHODS AND MEDIA FOR ESTIMATING COMPENSATORY RESERVE AND PREDICTING HEMODYNAMIC DECOMPENSATION USING PHYSIOLOGICAL DATA

(71) Applicants: Mayo Foundation for Medical Education and Research, Rochester, MN (US); The Government of The United States, as Represented by the Secretary of the Army, Frederick, MD (US)

(72) Inventors: Robert W. Techentin, Rochester, MN (US); Timothy B. Curry, Rochester, MN (US); Michael J. Joyner, Rochester, MN (US); Clifton R. Haider, Rochester, MN (US); David R. Holmes, III, Rochester, MN (US); Christopher L. Felton, Rochester, MN (US); Barry K. Gilbert, Rochester, MN (US); Charlotte Sue Van Dorn, Rochester, MN (US); William A. Carey, Rochester, MN (US); Victor A. Convertino, San Antonio, TX (US)

(73) Assignees: Mayo Foundation for Medical Education and Research, Rochester, MN (US); The Government of the United States, as Represented by the Secretary of the Army, Frederick, MD (US)

( * ) Notice: Subject to any disclaimer, the term of this patent is extended or adjusted under 35 U.S.C. 154(b) by 117 days.

(21) Appl. No.: 16/934,805

(22) Filed: Jul. 21, 2020

(65) Prior Publication Data
US 2021/0022620 A1    Jan. 28, 2021

Related U.S. Application Data

(60) Provisional application No. 62/877,145, filed on Jul. 22, 2019.

(51) Int. Cl.
*A61B 5/02* (2006.01)
*A61B 5/00* (2006.01)
(Continued)

(52) U.S. Cl.
CPC ........ *A61B 5/02042* (2013.01); *A61B 5/0004* (2013.01); *A61B 5/02028* (2013.01);
(Continued)

(58) Field of Classification Search
CPC ............. A61B 5/02042; A61B 5/0004; A61B 5/02028; A61B 5/02108; A61B 5/02416;
(Continued)

(56) References Cited

U.S. PATENT DOCUMENTS

| 11,382,571 B2 * | 7/2022 | Mulligan | ............. A61B 5/7246 |
| 2012/0330117 A1 * | 12/2012 | Grudic | ................... G16H 50/30 |
| | | | 600/323 |

(Continued)

OTHER PUBLICATIONS

Zhao et al., "Convolutional neural networks for time series classification," in Journal of Systems Engineering and Electronics, vol. 28, No. 1, pp. 162-169, Feb. 2017 (Year: 2017).*

(Continued)

*Primary Examiner* — Miranda M Huang
*Assistant Examiner* — Yao David Huang
(74) *Attorney, Agent, or Firm* — Quarles & Brady LLP

(57) ABSTRACT

In accordance with some embodiments, systems, methods, and media for estimating compensatory reserve and predicting hemodynamic decompensation using physiological data are provided. In some embodiments, a system for estimating compensatory reserve is provided, the system comprising: a
(Continued)

processor programmed to: receive a blood pressure waveform of a subject; generate a first sample of the blood pressure waveform with a first duration; provide the sample as input to a trained CNN that was trained using samples of the first duration from blood pressure waveforms recorded from subjects while decreasing the subject's central blood volume, each sample being associated with a compensatory reserve metric; receive, from the trained CNN, a first compensatory reserve metric based on the first sample; and cause information indicative of remaining compensatory reserve to be presented.

14 Claims, 15 Drawing Sheets

(51) Int. Cl.
| | |
|---|---|
| A61B 5/021 | (2006.01) |
| A61B 5/024 | (2006.01) |
| G06N 3/004 | (2023.01) |
| G06N 3/008 | (2023.01) |

(52) U.S. Cl.
CPC ...... *A61B 5/02108* (2013.01); *A61B 5/02416* (2013.01); *A61B 5/7264* (2013.01); *A61B 5/7275* (2013.01); *G06N 3/004* (2013.01); *G06N 3/008* (2013.01)

(58) Field of Classification Search
CPC .... A61B 5/7264; A61B 5/7275; G06N 3/004; G06N 3/008
See application file for complete search history.

(56) References Cited

U.S. PATENT DOCUMENTS

| | | | | |
|---|---|---|---|---|
| 2015/0374300 | A1* | 12/2015 | Najarian | G16Z 99/00 702/19 |
| 2016/0038042 | A1* | 2/2016 | Mulligan | A61B 5/031 600/371 |
| 2017/0281020 | A1* | 10/2017 | Mulligan | G16H 50/70 |
| 2018/0032689 | A1* | 2/2018 | Kiranyaz | G16H 50/20 |
| 2019/0114546 | A1* | 4/2019 | Anil | G06N 3/084 |
| 2019/0139563 | A1* | 5/2019 | Chen | G10L 21/0216 |
| 2019/0333643 | A1* | 10/2019 | Villongco | A61B 5/319 |

OTHER PUBLICATIONS

Taghipour et al., "A Neural Approach to Automated Essay Scoring," Proceedings of the 2016 Conference on Empirical Methods in Natural Language Processing, pp. 1882-1891, Austin, Texas, Nov. 1-5, 2016 (Year: 2016).*

Janak et al., "Predictors of the Onset of Hemodynamic Decompensation During Progressive Central Hypovolemia: Comparison of the Peripheral Perfusion Index, Pulse Pressure Variability, and Compensatory Reserve Index." Shock: Injury, Inflammation, and Sepsis: Lab. and Clinical Approaches 44(6):p. 548-553 (Year: 2015).*

Saglani, Vatsal, "Multi-class Image classification with CNN usingPyTorch, and the basics of Convolutional NeuralNetwork". Medium, Jun. 27, 2019. Retrieved from <https://thevatsalsaglani.medium.com/multi-class-image-classification-using-cnn-over-pytorch-and-the-basics-of-cnn-fdf425a11dc0> (Year: 2019).*

Guo et al., "A deep learning-based method for relative location prediction in CT scan images". arXiv:1711.07624v1 [cs.CV] Nov. 21, 2017 (Year: 2017).*

"1.17. Neural network models (supervised)," Scikit-learn. Archived Apr. 17, 2019. Retrieved on Jun. 24, 2023. Retrieved from <https://web.archive.org/web/20190417113131/https://scikit-learn.org/stable/modules/neural_networks_supervised.html> (Year: 2019).*

Kiranyaz et al., "1D Convolutional Neural Networks and Applications: A Survey," arXiv:1905.03554v1 [eess.SP] May 9, 2019 (Year: 2019).*

Convertino et al., "AI-Enabled Advanced Development for Assessing Low Circulating Blood Volume for Emergency Medical Care: Comparison of Compensatory Reserve Machine-Learning Algorithms," Sensors 2022, 22, 2642 (Year: 2022).*

Fu et al., "Towards end-to-end pulsed eddy current classification and regression with CNN," 2019 IEEE International Instrumentation and Measurement Technology Conference (I2MTC), Auckland, New Zealand, 2019, pp. 1-5, doi: 10.1109/I2MTC.2019.8826858. (Year: 2019).*

Ballinger GA, "Using generalized estimating equations for longitudinal data analysis," Organizational research methods, vol. 7, No. 2, pp. 127-150, 2004.

Bennis, F. C., et al. "A machine-learning based analysis for the recognition of progressive central hypovolemia." Physiological Measurement 38.9 (2017): 1791.

Benov, A et al, "The effect of blood transfusion on compensatory reserve: A prospective clinical trial," Journal of Trauma and Acute Care Surgery, vol. 83, No. 1, pp. S71-S76, 2017.

Bergstra, J et al, "Making a science of model search: Hyperparameter optimization in hundreds of dimensions for vision architectures," 2013.

Boucek MM, et al. Registry for the International Society for Heart and Lung Transplantation: seventh official pediatric report—2004. J Heart Lung Transplant. 2004;23:933-947.

Carrico, CJ et al, "Scientific priorities and strategic planning for resuscitation research and life saving therapy following traumatic injury: report of the pulse trauma work group," Academic emergency medicine, vol. 9, No. 6, pp. 621-626, 2002.

Connolly D, et al. The New York University Pediatric Heart Failure Index: a new method of quantifying chronic heart failure severity in children. J Pediatr. 2001;138:644-648.

Convertino, VA et al, "Estimation of individual-specific progression to impending cardiovascular instability using arterial waveforms," Journal of Applied Physiology, vol. 115, No. 8, pp. 1196-1202, 2013.

Convertino, VA et al, "Individual-specific, beat-to-beat trending of significant human blood loss: the compensatory reserve," Shock, vol. 44, pp. 27-32, 2015.

De Mos N, et al. Pediatric in-intensive-care unit cardiac arrest: incidence, survival, and predictive factors. Crit Care Med. 2006;34:1209-15.

Hatib, F., et al. "Machine-learning algorithm to predict hypotension based on high-fidelity arterial pressure waveform analysis." Anesthesiology: The Journal of the American Society of Anesthesiologists 129.4 (2018): 663-674.

Howard, JT et al, "Specificity of compensatory reserve and tissue oxygenation as early predictors of tolerance to progressive reductions in central blood volume," Shock, vol. 46, No. 3S, pp. 68-73, 2016.

Hunt SA, et al. ACC/AHA guidelines for the evaluation and management of chronic heart failure in the adult: executive summary: a report of the American College of Cardiology/American Heart Association Task Force on Practice Guidelines. (Committee to Revise the 1995 Guidelines for the Evaluation and Management of Heart Failure). Circulation. 2001;104:2996-3007.

Ioffe S et al, "Batch normalization: Accelerating deep network training by reducing internal covariate shift," arXiv preprint arXiv:1502.03167, 2015.

Janak, JC et al, "Predictors of the onset of hemodynamic decompensation during progressive central hypovolemia: comparison of the peripheral perfusion index, pulse pressure variability, and compensatory reserve index," Shock, vol. 44, No. 6, pp. 548-553, 2015.

Ji, S-Y et al, "Wavelet based analysis of physiological signals for prediction of severity of hemorrhagic shock," in Complex Medical Engineering, 2009. CME. ICME International Conference on. IEEE, 2009, pp. 1-6.

Johnson, MC et al. "Comparison of compensatory reserve and arterial lactate as markers of shock and resuscitation." Journal of Trauma and Acute Care Surgery 83.4 (2017): 603-608.

(56) References Cited

OTHER PUBLICATIONS

Johnson, MC et al., "Compensatory reserve index: performance of a novel monitoring technology to identify the bleeding trauma patient," Shock, vol. 49, No. 3, pp. 295-300, 2018.
Kay JD, et al. Congestive heart failure in pediatric patients. Am Heart J. 2001;142:923-928.
Lipshultz SE, et al. The incidence of pediatric cardiomyopathy in two regions of the United States. N Engl J Med. 2003;348:1647-1655.
Lipshultz SE. Ventricular dysfunction clinical research in infants, children and adolescents. Prog Pediatr Cardiol. 2000;12:1-28.
Litjens, G et al, "A survey on deep learning in medical image analysis," Medical image analysis, vol. 42, pp. 60-88, 2017.
Massidda B, et al. Early detection of the anthracycline-induced cardiotoxicity. A non-invasive haemodynamic study. Anticancer Res. Jan.-Feb. 1997;17:663-8.
Moulton, SL et al, "Running on empty? the compensatory reserve index," Journal of Trauma and Acute Care Surgery, vol. 75, No. 6, pp. 1053-1059, 2013.
Nadler, R et al, "The value of noninvasive measurement of the compensatory reserve index in monitoring and triage of patients experiencing minimal blood loss," Shock, vol. 42.2, pp. 93-98, 2014.
Ross RD, et al. Grading the severity of congestive heart failure in infants. Pediatr Cardiol. 1992;13:72-75.
Schiller, AM et al, "The physiology of blood loss and shock: New insights from a human laboratory model of hemorrhage," Experimental Biology and Medicine, vol. 242, No. 8, pp. 874-883, 2017.
SOLVD Investigators, et al. Effect of enalapril on mortality and the development of heart failure in asymptomatic patients with reduced left ventricular ejection fractions. N Engl J Med. Sep. 3, 1992;327:685-91.
Stewart, CL et al, "Detection of low-volume blood loss: compensatory reserve versus traditional vital signs," Journal of Trauma and Acute Care Surgery, vol. 77, No. 6, pp. 892-898, 2014.
Szegedy, C et al, "Inception-v4, inception-resnet and the impact of residual connections on learning." in AAAI, vol. 4, 2017, p. 12.
Van Der Ster, BJP, et al. "Detecting central hypovolemia in simulated hypovolemic shock by automated feature extraction with principal component analysis." Physiological reports 6.22 (2018): e13895.
Van Der Ster, BJP, et al. "Support vector machine based monitoring of cardio-cerebrovascular reserve during simulated hemorrhage." Frontiers in physiology 8 (2018): 1057.

\* cited by examiner

TABLE I
Hyper Parameter Values for CRM CNN

| Parameter | Value |
|---|---|
| First Conv Layer Filters | 12 |
| First Conv Layer Kernel Size | 6 |
| First Conv Layer Pool Size | 4 |
| Number of Conv/Pool Layers | 7 |
| Conv Filters Start | 6 |
| Conv Filters Multiplier | 1.50 |
| Conv Kernel Size | 12 |
| Conv Pool Size | 3 |
| Residual Layers | None |
| FC Layer 1 Units | 565 |
| FC Layer 2 Units | 517 |
| L2 Weight Regularization | 0.00037 |
| Learning Rate | 0.000135 |
| Batch Size | 100 |

FIG. 6

SYSTEMS, METHODS AND MEDIA FOR ESTIMATING COMPENSATORY RESERVE AND PREDICTING HEMODYNAMIC DECOMPENSATION USING PHYSIOLOGICAL DATA

CROSS-REFERENCE TO RELATED APPLICATIONS

This application is based on, claims the benefit of, and claims priority to U.S. Provisional Application No. 62/877,145, filed Jul. 22, 2019, which is hereby incorporated herein by reference in its entirety for all purposes.

STATEMENT REGARDING FEDERALLY SPONSORED RESEARCH

This invention was made with government support under N66001-12-D-0088 awarded by the U.S. Department of Defense. The government has certain rights in the invention.

BACKGROUND

Hemorrhage is the leading cause of death from trauma. While early intervention to prevent hemodynamic collapse can reduce the risk of death from hemorrhage, it is difficult to determine how much blood has been lost and how close a particular patient is to hemodynamic collapse as individuals respond differently to similar amounts of blood loss. Determining when hemodynamic collapse is likely to occur is, in part, complicated by physiologic mechanisms that compensate for blood loss, which can help maintain, or nearly maintain, standard vital signs such as systolic blood pressure despite ongoing blood loss. However, these mechanisms are not easily measured and after a threshold amount of blood loss begin to lose effectiveness quickly leading from a seemingly stable condition to one in which the patient is in imminent danger of death.

Accordingly, systems, methods, and media for estimating compensatory reserve and predicting hemodynamic decompensation using physiological data are desirable.

SUMMARY

In accordance with some embodiments of the disclosed subject matter, systems, methods, and media for estimating compensatory reserve and predicting hemodynamic decompensation using physiological data are provided.

In accordance with some embodiments of the disclosed subject matter, a system for estimating compensatory reserve is provided, the system comprising: at least one hardware processor that is programmed to: receive a blood pressure waveform of a subject; generate a first sample of the blood pressure waveform, wherein the first sample comprises a time series of blood pressure values having a first duration; provide the sample as input to a trained convolutional neural network (CNN), wherein the CNN was trained using samples of the first duration from blood pressure waveforms recorded from a plurality of subjects while decreasing the subject's central blood volume, and wherein each sample was associated with a compensatory reserve metric based on a decrease of the subject's central blood volume at the time the sample was recorded; receive, from the trained CNN, a first compensatory reserve metric based on the first sample; and cause information indicative of remaining compensatory reserve to be presented.

In some embodiments, the first duration is in a range of 2 seconds to 30 seconds.

In some embodiments, the first duration is 20 seconds.

In some embodiments, the trained CNN is a 1 dimensional CNN.

In some embodiments, the output layer of the trained CNN is a linear layer.

In some embodiments, the blood pressure waveforms were recorded while varying amounts of negative pressure were applied to each subject's lower body.

In accordance with some embodiments of the disclosed subject matter, a method for estimating compensatory reserve is provided, the method comprising: receiving a blood pressure waveform of a subject; generating a first sample of the blood pressure waveform, wherein the first sample has a first duration; providing the sample as input to a trained convolutional neural network (CNN), wherein the CNN was trained using samples of the first duration from blood pressure waveforms recorded from a plurality of subjects while decreasing the subject's central blood volume, and wherein each sample was associated with a compensatory reserve metric based on a decrease of the subject's central blood volume at the time the sample was recorded; receiving, from the trained CNN, a first compensatory reserve metric based on the first sample; and causing information indicative of remaining compensatory reserve to be presented.

In some embodiments, a device for recording physiological signals is provided, the device comprising: an enclosure having dimensions no greater than 35×35×13 mm; a circuit board; a sensor transducer board coupled to the circuit board; a non-volatile memory coupled to the circuit board; and at least one processor that is coupled to the circuit board, wherein the at least one processor is programmed to: receive, via the sensor transducer board, a first signal from a first physiological sensor; generate a multiplicity of samples of the first signal at a first sampling rate; generate a metric based on the signal; and cause the multiplicity of samples and the metric to be stored using the non-volatile memory.

In some embodiments, the first sampling rate is at least 1000 samples per second.

In some embodiments, the first physiological sensor is a photoplethysmography sensor, and the first signal is a blood pressure waveform.

In some embodiments, the at least one processor is further programmed to: receive, via the sensor transducer board, a second signal from a second physiological sensor; generate a second multiplicity of samples of the second signal at the first sampling rate; generate a second metric based on the signal; and cause the second multiplicity of samples and the metric to be stored using the non-volatile memory.

In some embodiments, the at least one processor is further programmed to: generate a first time series of the blood pressure waveform using the multiplicity of samples, wherein the first time series has a first duration; provide the first time series as input to a trained convolutional neural network (CNN), wherein the CNN was trained using a plurality of time series of the first duration from blood pressure waveforms recorded from a plurality of subjects while decreasing the subject's central blood volume, and wherein each time series of the plurality of time series was associated with a compensatory reserve metric based on a decrease of the subject's central blood volume at the time the sample was recorded; receive, from the trained CNN, the metric based on the first time series; and cause information indicative of remaining compensatory reserve to be stored as the metric.

In some embodiments, the device further comprises a wireless interface, wherein the at least one processor is further programmed to cause the wireless interface to transmit the metric to a computing device.

In some embodiments, the processor comprises an application-specific integrated circuit (ASIC), and wherein the at least one processor is programmed at least in part based on a configuration of logic gates in the ASIC.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 6 shows an example of a table of hyper parameter values that can be used to implement an effective convolutional neural network for estimating compensatory reserve and predicting hemodynamic decompensation using physiological data in accordance with some embodiments of the disclosed subject matter.

DETAILED DESCRIPTION

In accordance with various embodiments, mechanisms (which can, for example, include systems, methods, and media) for estimating compensatory reserve and predicting hemodynamic decompensation using physiological data are provided.

In some embodiments, the mechanisms described herein can generate a metric indicative of health status for trauma victims that can enable timely and effective treatment, particularly when medical resources are limited and patient triage must be prioritized. In some embodiments, the mechanisms described herein can be used to provide a computational model that can estimate a Compensatory Reserve Metric (CRM) using physiologic data, such as blood pressure waveforms. In some embodiments, the computational model can be realized by training deep Convolutional Neural Networks (CNNs). In some embodiments, deep CNNs can be used to automatically learn relevant features from waveforms used as training data, whereas conventional techniques often require significant feature engineering, painstaking extraction of dozens, hundreds or even thousands of biological or statistical parameters from the waveforms. While CNNs have been successful in recent years at generalized image classification tasks, this has required training datasets of hundreds of thousands to millions of images, and results in 2D or 3D networks that are inappropriate for tasks such as analyzing 1D waveforms generated from physiologic data. Unlike generalized image classification, in which billions of examples exist that need only be labeled (e.g., by a human), such data is much more difficult to generate for traumatic injuries in which the ground truth is unknown. For example, even if blood pressure data of trauma victims were available from the time that the trauma occurred until hemodynamic decompensation occurred, it would be difficult or impossible to label the data with sufficiently fine-grained labels to train a reliable computational model. In some embodiments, the mechanisms described herein can use relatively few examples (e.g., a dataset from only hundreds of human subjects) of labeled data to train an effective computation model for estimating CRM and predicting hemodynamic decompensation.

Figure 1:
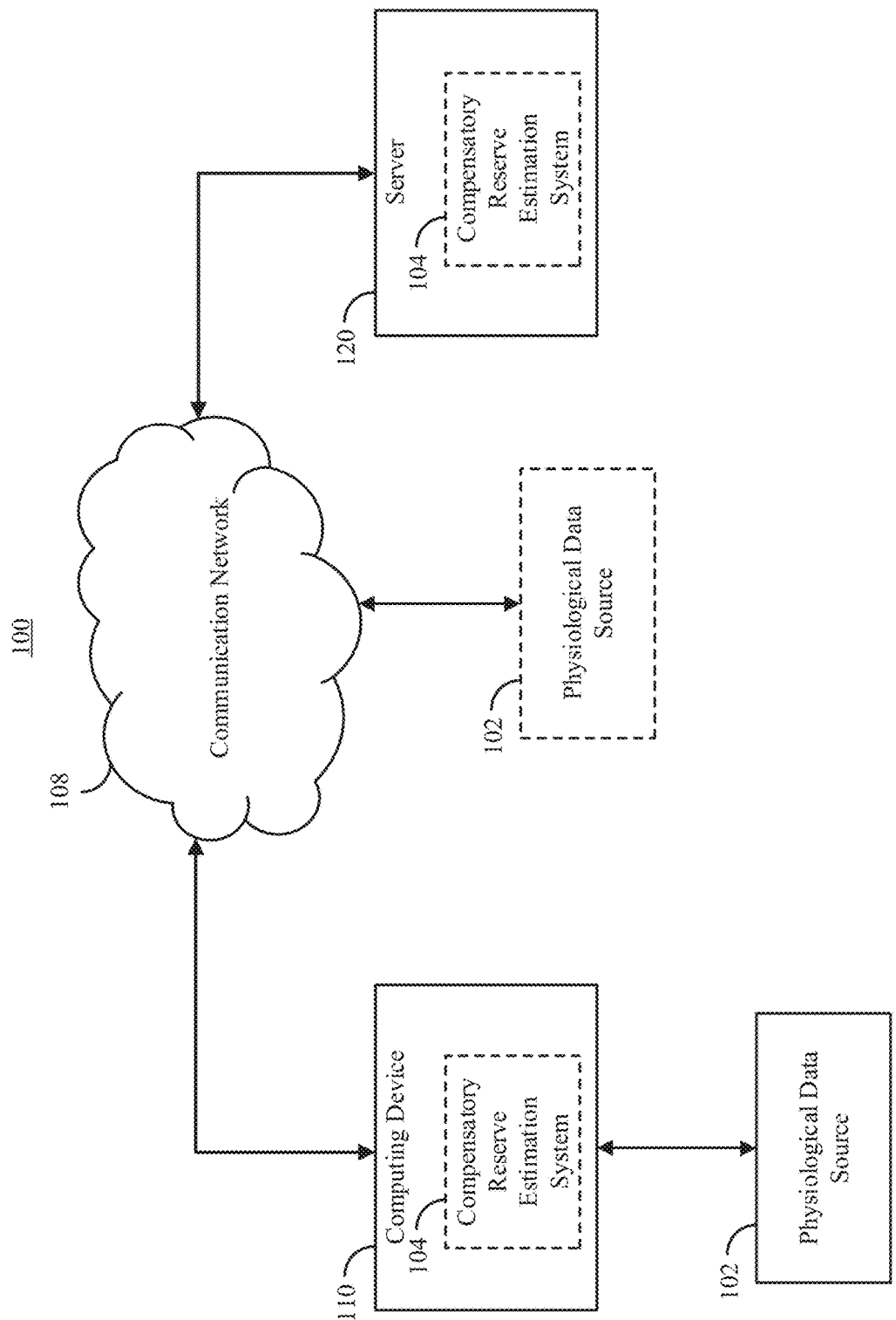
FIG. 1 shows an example of a system for estimating compensatory reserve and predicting hemodynamic decompensation using physiological data in accordance with some embodiments of the disclosed subject matter.

FIG. 1 shows an example 100 of a system for estimating compensatory reserve and predicting hemodynamic decompensation using physiological data in accordance with some embodiments of the disclosed subject matter. As shown in FIG. 1, a computing device 110 can receive physiologic data from a physiological data source 102 that outputs of one or more types of physiological data. In some embodiments, computing device 110 can execute at least a portion of a compensatory reserve estimation system 104 to automatically estimate a compensatory reserve metric from the physiological data and/or predict an onset of hemodynamic decompensation.

Additionally or alternatively, in some embodiments, computing device 110 can communicate information about physiological data from physiological data source 102 to a server 120 over a communication network 108, which can execute at least a portion of compensatory reserve estimation system 104 to automatically estimate a compensatory reserve metric from the physiological data and/or predict an onset of hemodynamic decompensation. In such embodiments, server 120 can return information to computing device 110 (and/or any other suitable computing device) indicative of a compensatory reserve estimate and/or predictive of the onset of hemodynamic decompensation.

In some embodiments, computing device 110 and/or server 120 can be any suitable computing device or combination of devices, such as a desktop computer, a laptop computer, a smartphone, a tablet computer, a wearable computer, a server computer, a virtual machine being executed by a physical computing device, etc. As described below in connection with FIGS. 3-10, in some embodiments, computing device 110 and/or server 120 can receive labeled physiological data (e.g., a blood pressure waveform) from one or more sources of physiological data (e.g., physiological data source 102), and can extract a sample physiological data waveform (e.g., covering a particular period of time, such as a time period of any length of time in a range of 5 seconds to several minutes, 10 seconds to one minute, 15 seconds to 45 seconds, 20 second to 30 seconds, etc.), and label the sample waveform using an inferred compensatory reserve metric determined based on the labeling data for the entire original waveform from which the sample was extracted. In some embodiments, compensatory reserve estimation system 104 can use the labeled sample waveform (and other labeled sample waveforms) to train a 1D CNN to classify an unlabeled sample waveform as corresponding to a particular compensatory reserve level In some embodiments, compensatory reserve estimation system 104 can receive unlabeled physiological data (e.g., a blood pressure waveform) from one or more sources of physiological data (e.g., physiological data source 102), and can extract a sample physiological data waveform (e.g., covering a particular period of time, such as a time period of any length of time in a range of 5 seconds to several minutes, 10 seconds to one minute, 15 seconds to 45 seconds, 20 second to 30 seconds, etc.) and provide the sample waveform to the trained CNN for analysis. In some embodiments, compensatory reserve estimation system 104 can generate a CRM and/or a prediction of the onset of hemodynamic decompensation, and display the results for a user (e.g., a physician, a nurse, a paramedic, etc.).

In some embodiments, physiological data source 102 can be any suitable source of physiological data, such as a plethysmograph. In some embodiments, physiological data source 102 can be local to computing device 110. For example, physiological data source 102 can be incorporated with computing device 110 (e.g., physiological data source 110 can be one or more sensors that are integrated into computing device 110). As another example, physiological data source 102 can be connected to computing device 110 by a cable, a direct wireless link, etc. Additionally or alternatively, in some embodiments, physiological data source 102 can be located locally and/or remotely from computing device 110, and can communicate physiological data to computing device 110 (and/or server 120) via a communication network (e.g., communication network 108).

In some embodiments, communication network 108 can be any suitable communication network or combination of communication networks. For example, communication network 108 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

Figure 2:
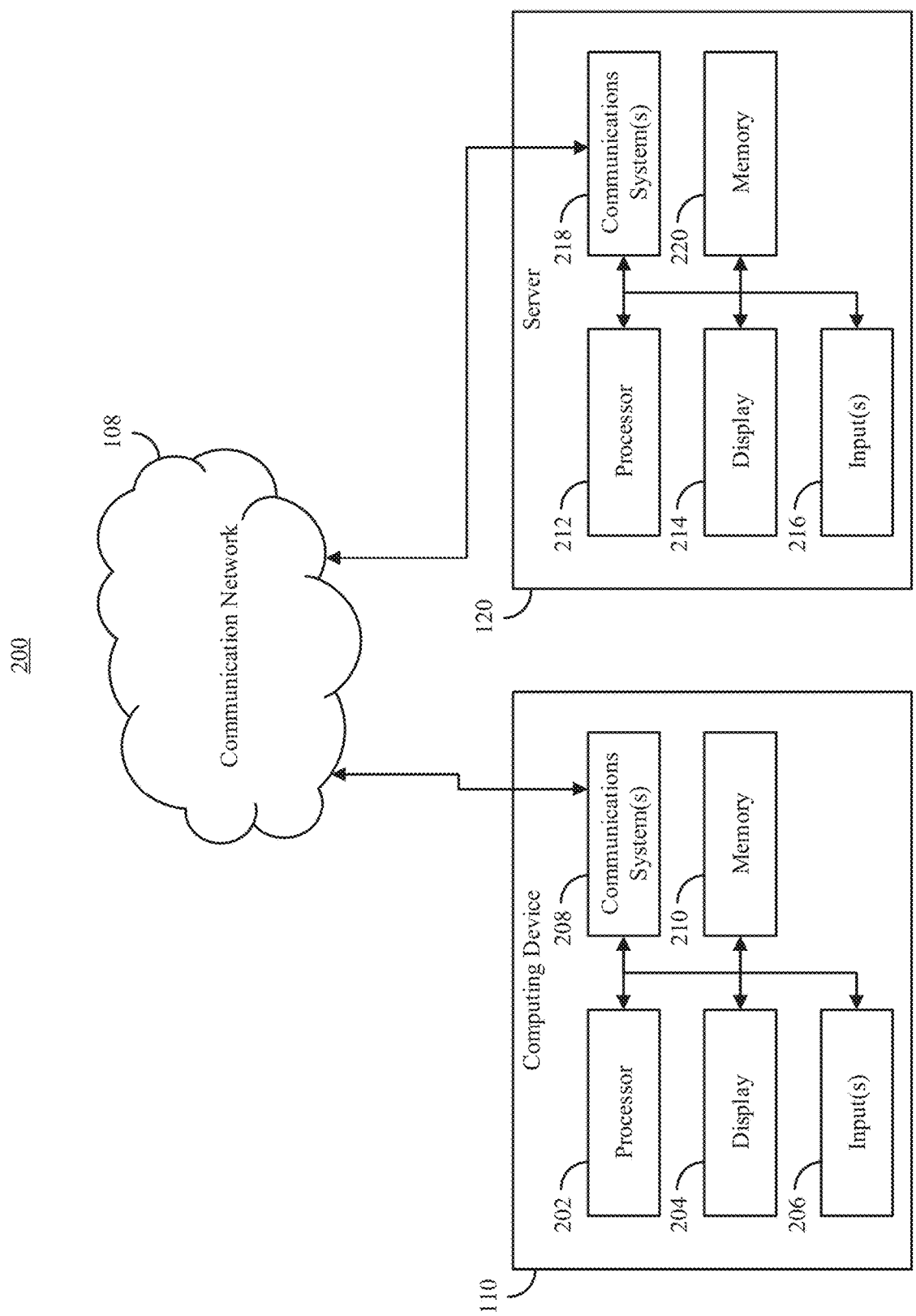
FIG. 2 shows an example of hardware that can be used to implement a computing device, and a server, shown in FIG. 1 in accordance with some embodiments of the disclosed subject matter.

FIG. 2 shows an example 200 of hardware that can be used to implement computing device 110, and/or server 120 in accordance with some embodiments of the disclosed subject matter. As shown in FIG. 2, in some embodiments, computing device 110 can include a processor 202, a display 204, one or more inputs 206, one or more communication systems 208, and/or memory 210. In some embodiments, processor 202 can be any suitable hardware processor or combination of processors, such as a central processing unit (CPU), a graphics processing unit (GPU), a microcontroller (MCU), an application specification integrated circuit (ASIC), a field programmable gate array (FPGA), etc. In some embodiments, display 204 can include any suitable display devices, such as a computer monitor, a touchscreen, a television, etc. In some embodiments, inputs 206 can include any suitable input devices and/or sensors that can be used to receive user input, such as a keyboard, a mouse, a touchscreen, a microphone, etc.

In some embodiments, communications systems 208 can include any suitable hardware, firmware, and/or software for communicating information over communication network 108 and/or any other suitable communication networks. For example, communications systems 208 can include one or more transceivers, one or more communication chips and/or chip sets, etc. In a more particular example, communications systems 208 can include hardware, firmware and/or software that can be used to establish a Wi-Fi connection, a Bluetooth connection, a cellular connection, an Ethernet connection, etc.

In some embodiments, memory 210 can include any suitable storage device or devices that can be used to store instructions, values, etc., that can be used, for example, by processor 202 to present content using display 204, to communicate with server 120 via communications system(s) 208, etc. Memory 210 can include any suitable volatile memory, non-volatile memory, storage, or any suitable combination thereof. For example, memory 210 can include RAM, ROM, EEPROM, one or more flash drives, one or more hard disks, one or more solid state drives, one or more optical drives, etc. In some embodiments, memory 210 can have encoded thereon a computer program for controlling operation of computing device 110. In such embodiments, processor 202 can execute at least a portion of the computer program to present content (e.g., physiological waveforms, user interfaces, graphics, tables, etc.), receive content from server 120, transmit information to server 120, etc.

In some embodiments, server 120 can include a processor 212, a display 214, one or more inputs 216, one or more communications systems 218, and/or memory 220. In some embodiments, processor 212 can be any suitable hardware processor or combination of processors, such as a CPU, a GPU, an MCU, an ASIC, an FPGA, etc. In some embodiments, display 214 can include any suitable display devices, such as a computer monitor, a touchscreen, a television, etc. In some embodiments, inputs 216 can include any suitable input devices and/or sensors that can be used to receive user input, such as a keyboard, a mouse, a touchscreen, a microphone, etc.

In some embodiments, communications systems 218 can include any suitable hardware, firmware, and/or software for communicating information over communication network 108 and/or any other suitable communication networks. For example, communications systems 218 can include one or more transceivers, one or more communication chips and/or chip sets, etc. In a more particular example, communications systems 218 can include hardware, firmware and/or software that can be used to establish a Wi-Fi connection, a Bluetooth connection, a cellular connection, an Ethernet connection, etc.

In some embodiments, memory 220 can include any suitable storage device or devices that can be used to store instructions, values, etc., that can be used, for example, by processor 212 to present content using display 214, to communicate with one or more computing devices 110, etc. Memory 220 can include any suitable volatile memory, non-volatile memory, storage, or any suitable combination thereof. For example, memory 220 can include RAM, ROM, EEPROM, one or more flash drives, one or more hard disks, one or more solid state drives, one or more optical drives, etc. In some embodiments, memory 220 can have encoded thereon a server program for controlling operation of server 120. In such embodiments, processor 212 can execute at least a portion of the server program to transmit information and/or content (e.g., physiologic data, information indicative of compensatory reserve, a user interface, etc.) to one or more computing devices 110, receive information and/or content from one or more computing devices 110, receive instructions from one or more devices (e.g., a personal computer, a laptop computer, a tablet computer, a smartphone, etc.), etc.

Figure 3:
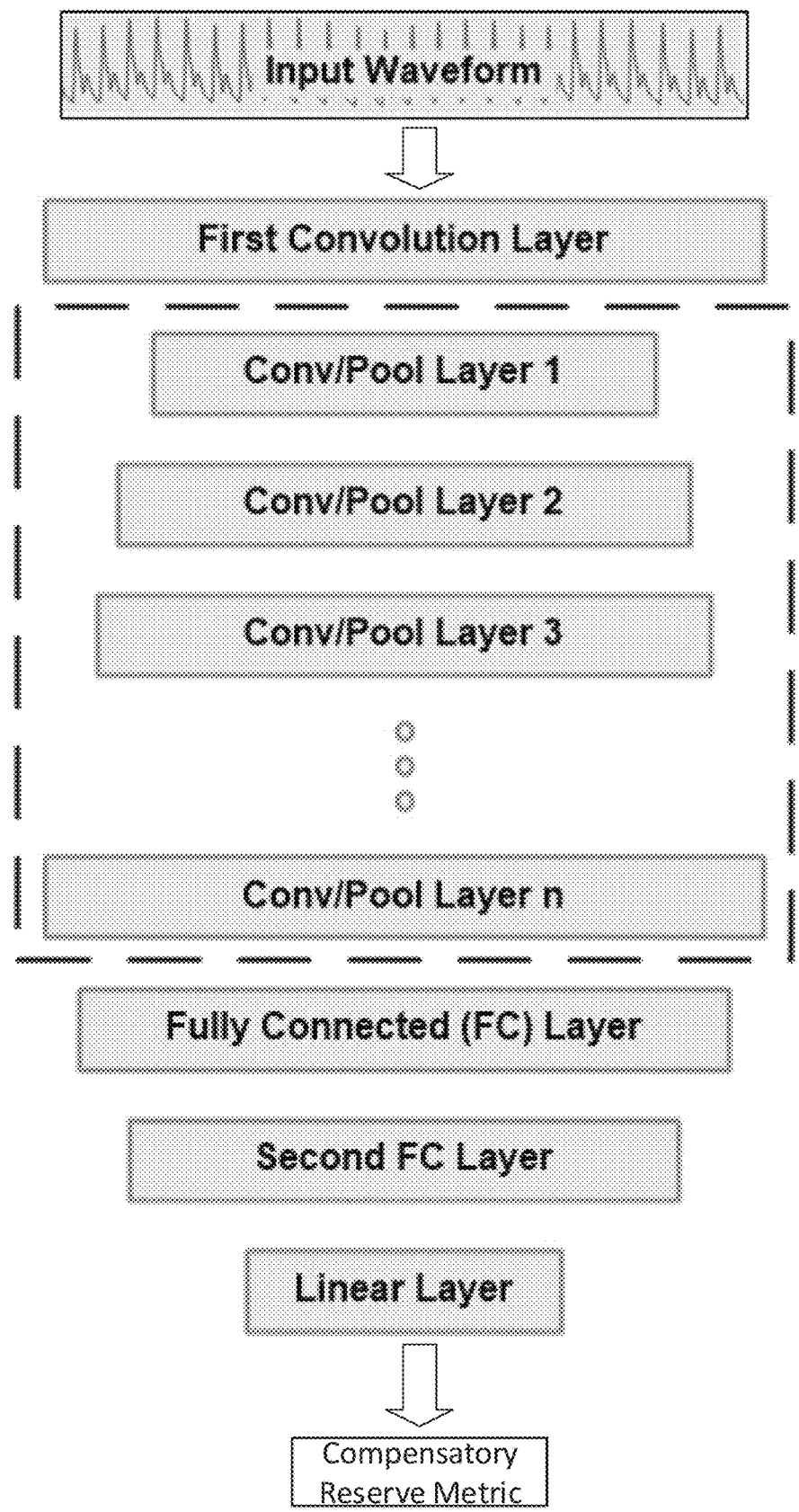
FIG. 3 shows an example architecture for a one dimensional convolutional neural network in accordance with some embodiments of the disclosed subject matter.

FIG. 3 shows an example architecture for a one dimensional convolutional neural network in accordance with some embodiments of the disclosed subject matter. Unlike in the field of image classification, there is not an existing corpus of CNN architectures appropriate for 1-D CNN analysis of biologic waveforms. Additionally, the best architectures for 1-D CNN analysis of biologic waveforms are not obvious. In general, a number of possible architectures can be explored using the hyperopt package to find relatively high performing values for the number of layers, numbers of filters, kernel sizes, and other parameters. Hyper-opt is a Python library for optimizing over awkward search spaces with real-valued, discrete, and conditional dimensions. In some embodiments, Tree of Parzen Estimators (TPE) can be used to explore a high dimensional parameter space, where discrete parameters can be random choice or random integer, and real-valued parameters can be derived from uniform, log, normal, or log-normal distributions. The layers and characteristics of the CNN can be defined in terms of a hyperspace of these parameters, employing the layer stack shown in FIG. 3. In some embodiments, CNNs can be trained and tested using Python and Keras, with the Tensorflow back end. The Keras library can facilitate relatively simple demonstrations of modestly complex CNN models that perform relatively well for predicting CRM from Lower Body Negative Pressure (LBNP) blood pressure waveforms, as described below in connection with FIG. 8.

In some embodiments, a portion of a physiological waveform, which can be at a relatively high data sample rate (e.g., 50, 100, 500, 1000, or 1,500 samples per second, which is generally higher than a conventional rate used to sample signals for physiologic attributes such as pulse rate), can be provided as input to the CNN. In some embodiments, the first convolutional layer can be defined separately from the other layers, to insure that it is adapted to specific characteristics of the waveform data, and may have different kernel size and stride from the rest of the CNN. As shown in FIG. 3, the bulk of the network is a block of convolutional/pooling layers, with the same kernel size and stride, and an increasing number of filters for each layer. Within this group, the convolution layer can be followed by batch normalization, and a residual layer, then parameterized pooling and dropout. In some embodiments, the convolution layer group can be followed by one or more fully connected layers and a final linear unit to compute CRM. In some embodiments, global model parameters can that can be varied include learning rate, L2 regularization factor, batch size, choice of optimizer, dropout probability, pooling type, and/or activation function.

Figure 4A:
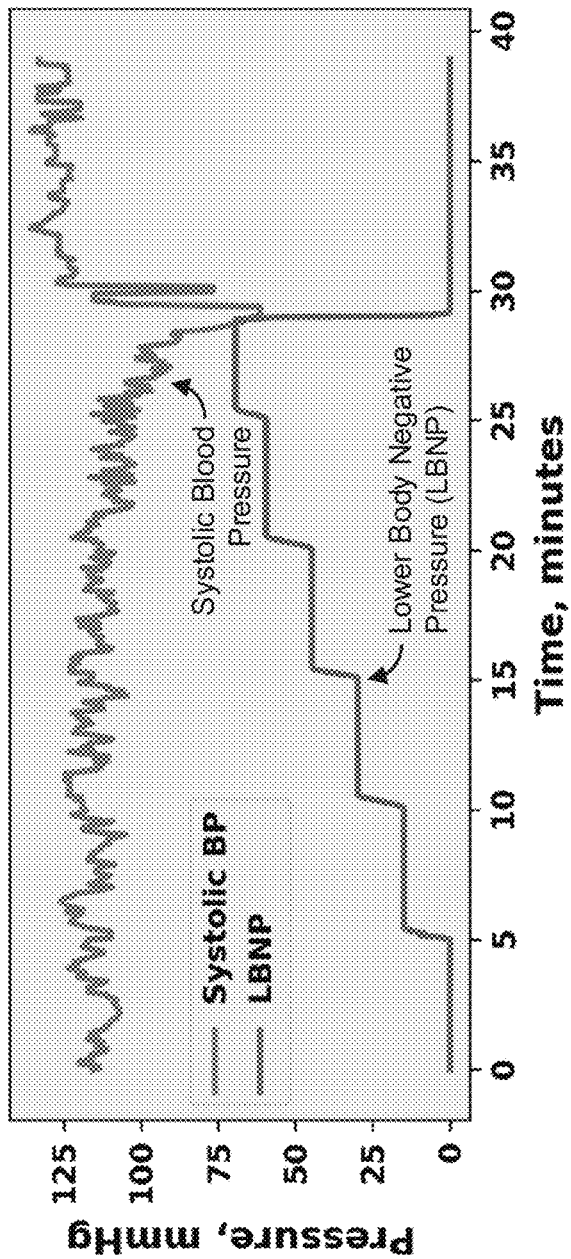
FIG. 4A shows an example of a labeled blood pressure waveform that can be used in connection with some embodiments of the disclosed subject matter.
Figure 4B:
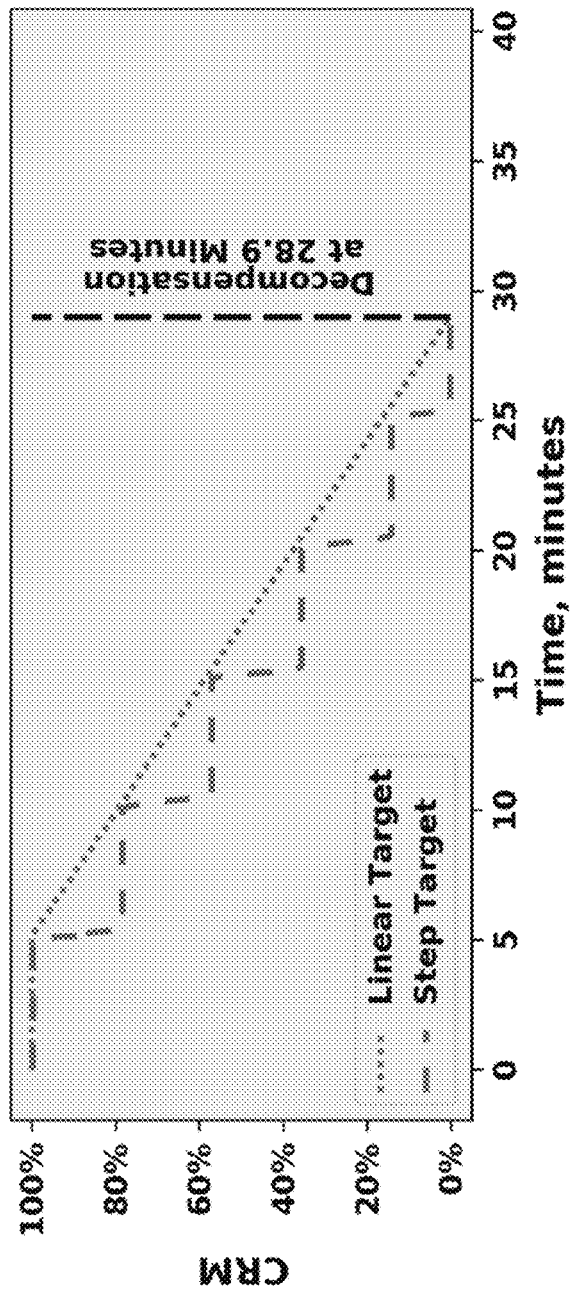
FIG. 4B shows an example of values of a compensatory reserve metric that can be inferred from the labeled blood pressure waveform of FIG. 4A in accordance with some embodiments of the disclosed subject matter.

FIG. 4A shows an example of a blood pressure attribute (systolic blood pressure), and experimentally applied LBNP that can be used in connection with some embodiments of the disclosed subject matter, and FIG. 4B shows an example of values of a compensatory reserve metric that can be inferred from the LBNP waveform of FIG. 4A in accordance with some embodiments of the disclosed subject matter. In some embodiments, a human model of hemorrhage can be used to generate data suitable for training a computation model to that estimates compensatory reserve and predicts hemodynamic decompensation using physiological data. In such embodiments, one or more Lower Body Negative Pressure (LBNP) techniques can be used to generate such data. For example, LBNP can include placing the lower half of a healthy test subject's body into a pressure chamber, which is then used to subject the subject's lower body to negative atmospheric pressure. This generally causes blood to be drawn to and/or trapped in the lower extremities, reducing central blood volume and emulating hemorrhage. When negative pressure is released, the subject's central blood volume quickly recovers. LBNP studies of hypovolemia have led to the development of the concept of Compensatory Reserve, the body's ability to compensate for blood loss. Compensatory Reserve is reported as 100% reserve for healthy individuals, down to 0% reserve at the point of hemodynamic decompensation.

The LBNP dataset was provided by the U.S. Army Institute of Surgical Research (USAISR) under a protocol approved by the Institutional Review Boards (IRBs) of both the USAISR and the Mayo Clinic. The dataset included physiologic recordings of 16 different signals from 222 subjects undergoing the LBNP protocol. Data for all subjects included continuous measurements of heart rate (HR) obtained from a standard lead-II electrocardiogram (ECG), peripheral capillary oxygen saturation (SpO2) obtained using a Near Infrared Spectroscopy (NIRS) system, capnogram (or end tidal CO2), the applied negative pressure in mmHg, and beat-to-beat systolic (SBP) and diastolic (DBP)

blood pressures, measured noninvasively using an infrared finger photoplethysmograph (PPG; Finometer® Blood Pressure Monitor, TNO-TPD Biomedical Instrumentation, Amsterdam, The Netherlands). The photoplethysmograph blood pressure cuff was placed on the middle finger of the left hand of each subject, which was laid at heart level and calibrated with a standard manual brachial blood pressure cuff. Recordings ranged from 9 to 60 minutes in duration with data acquired at 500 samples per second.

The experimental protocol applied progressively stepwise LBNP (e.g., as shown in FIG. 4A) while subjects were in a supine position. LBNP experiments began with five minutes of baseline recording, without application of LBNP (i.e., 0 mmHg), followed by five minute periods with chamber pressures set at 15, 30, 45, and 60 mmHg, with additional decreases of 10 mmHg every five minutes thereafter until the onset of hemodynamic decompensation. In accordance with the IRB, the maximum level of LBNP exposure was 5 minutes at 100 mmHg. No subject completed five minutes at 100 mmHg (i.e., all subjects reached hemodynamic decompensation before that point). For each subject, the experiment was ended at the point of decompensation, which was defined as systolic arterial pressure (SAP) falling below 80 mmHg (class III shock) concurrent with reporting of symptoms such as bradycardia, gray-out (loss of color vision), tunnel vision, sweating, nausea, and/or dizziness. Upon reaching this endpoint, the chamber vacuum was immediately released to ambient pressure, returning the subject to their baseline physiological status by rapidly restoring the central circulating blood volume.

FIG. 4A shows the applied stepwise LBNP and continuous systolic blood pressure (SBP) recordings obtained from the photoplethysmograph over the duration of the experiment for one subject. The SBP waveform shown in FIG. 4A highlights the difficulty of determining when hemodynamic compensation will occur without the aid of the mechanisms described herein. Shock is usually described clinically by severe hypotension (e.g., SBP<90 mmHg in adult subjects), though using this metric and similar standard vital signs can be misleading to the process of diagnosis. As shown in FIG. 4A, SBP remains relatively stable within normal clinical values over the course of progressive central hypovolemia, which can be ascribed to the bodies tight regulation of SBP by various compensatory mechanisms. Accordingly, SBP itself is a poor indicator of hemorrhage, and monitoring SBP is insufficient to provide adequate warning that a patient may be progressing toward hemodynamic decompensation) If the progression of hypovolemia is not arrested, the reserve to compensate is depleted and decompensation occurs. At decompensation, the SBP plummets (e.g., as shown starting around 27 or 28 minutes in FIG. 4A), signaling the exhaustion of compensatory feedback mechanisms. In some embodiments, tracking a signal that represents the underlying compensatory response provided by using the mechanisms described herein, a signal that changes immediately at the onset of blood loss, can assist a healthcare provider to avoid delays in recognition of the impending "crash" of SBP.

As shown in FIG. 4B, in some embodiments, the CRM at each point in time can be derived by fitting a line that starts at 100 during the baseline period and descends toward 0 at the time of decompensation. In some embodiments, stepwise values of CRM can be generated by dividing the decrease from 100 to 0 by the number of period weighted by the relative increase in LBNP (in mmHg) between each period. For example, as shown in FIG. 4B, five periods of increasing LBNP were applied after the initial baseline, with a total increase of 70 mmHG from the initial 0 mmHG. Accordingly, the first period can be labeled with a CRM of about 79 (e.g., a drop of $15/70 \times 100 = 21.42$), and the second can be labeled with a CRM of about 67, and so on.

Figure 5:
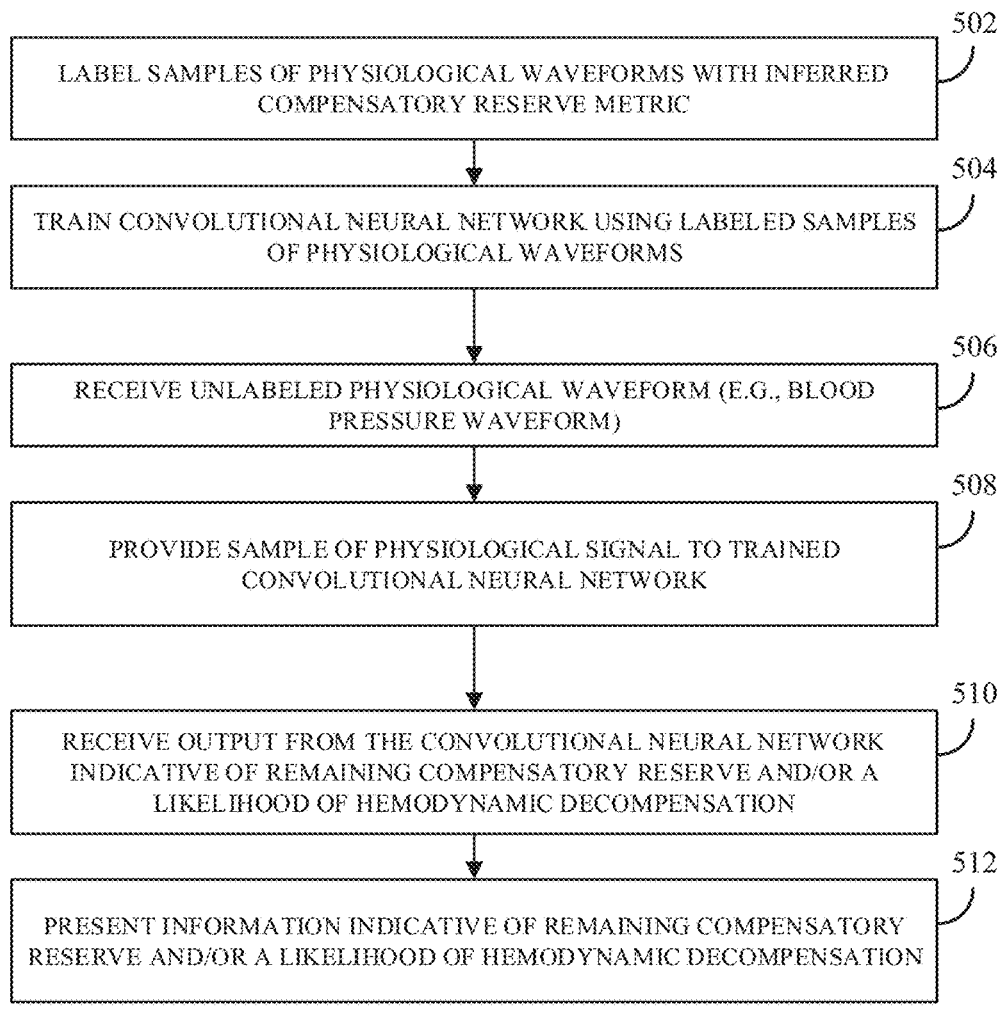
FIG. 5 shows an example 500 of a process for estimating compensatory reserve and predicting hemodynamic decompensation using physiological data in accordance with some embodiments of the disclosed subject matter.

FIG. 5 shows an example 500 of a process for estimating compensatory reserve and predicting hemodynamic decompensation using physiological data in accordance with some embodiments of the disclosed subject matter. At 502, process 500 can include labeling samples of physiological waveforms with an inferred compensatory reserve metric. For example, as shown in FIG. 4B, each waveform segment can be labeled using a linear approximation of CRM determined by fitting a straight line from the onset of LBNP (e.g., at 5 minutes) to the point of decompensation (e.g., when SBP falls below 80 mmHG and/or certain symptoms are reported and/or observed, as described above in connection with FIG. 4A). As another example, as shown in FIG. 4B, each waveform can be labeled using a stepwise approximation of CRM based on the periods at which pressure was increased.

At 504, process 500 can train a convolutional neural network using labeled samples of physiological waveforms. In some embodiments, process 500 can generate an architecture of a CNN and/or train the CNN using any suitable technique or combination of techniques. For example, process 500 can divide the data from various test subjects into training and test sets, respectively. In a more particular example, in a process implemented in accordance with some embodiments of the disclosed subject matter, data from 216 subjects was divided into training and test sets of 194 and 22, respectively.

In some embodiments, defining training and test in terms of individual subjects can be necessary to avoid over fitting (high variance) in cases where validation waveforms were selected from the pool of all subjects (e.g., if each waveform were converted to samples of a particular length and then all of the samples were divided into training and test datasets some of the waveforms in the test set may be very similar to waveforms in the training set which can give results indicating better performance than would be observed with novel data). In some embodiments, process 500 can use the training and test sets to train machine learning regression models to estimate CRM, in the range of 100% at baseline down to 0% at decompensation, using the labeled blood pressure waveform samples.

In some embodiments, process 500 can use a training target to perform supervised training of a regression model to estimate CRM, which can be calculated from the experimental data. Note that compensatory reserve cannot be directly measured, but CRM training targets can be defined from the experimental data, defining the subject's CRM as 100% during the first five minutes of baseline recordings (i.e., LBNP of 0 mmHg) and defining CRM as 0% at the point of decompensation. For example, this can exploit a key feature of an experimental dataset based on LBNP techniques, in which all subjects were taken to the point of decompensation, discovering their individual tolerance to LBNP. With the endpoints defined, each point in time can be labeled with a target CRM for supervised machine learning. As described above in connection with FIGS. 4A and 4B, process 500 can model decreasing CRM as a linear function over the duration of the LBNP experiment, or as a series of steps corresponding to the applied LBNP. For example, linear and stepped training targets for subject A157 are plotted in FIG. 4B, along with the corresponding applied LBNP and SBP in FIG. 4A. The point of decompensation at 28.9 minutes was derived from the release of LBNP. Note that the model was trained only on data before decompensation, as the target CRM cannot be inferred accurately during recovery due to the unknown rate at which the patient's CRM returned to 100%.

In some embodiments, after defining the endpoint and training targets, process 500 can truncate the recorded waveforms to the experiment length and divide into equal segments. For example, segments lengths of 20 seconds can capture several heart beats and respiration cycles. However, this is merely an example, and shorter or longer segment lengths can be used in some embodiments.

In some embodiments, process 500 can associate each waveform segment with a step-wise CRM training target. Additionally, in some embodiments, process 500 can associate each waveform segment with the subject identifier and a binary flag marking the point of decompensation. These data points can be used for post-training analysis to compute area under the receiver operating characteristic curve using the Generalized Estimating Equation approach (GEE).

In a particular example, training data resulting from 216 subjects included 30,075 training sample waveforms and 3,290 testing samples, based on the 194 and 22 subjects in the training and test sets, respectively. In some embodiments, as each waveform sample is a one-dimensional time series data structure, process 500 can train 1-D Convolutional Neural Networks (CNNs) to classify such data. In some embodiments, process 500 can train a CNN using 90% of the training set as training data, and 10% of the training set for validation. In some embodiments, process 500 can use any suitable loss function during training of the CNN. For example, process 500 can use a mean squared error (MSE) loss function that compares the predicted CRM to the training target for each waveform segment.

At 506, process 500 can receive an unlabeled physiological waveform. For example, in some embodiments, process 500 can receive a blood pressure waveform from a photoplethysmograph.

At 508, process 500 can generate an appropriate sample of the waveform and provide the sample to the trained CNN. For example, process 500 can generate a sample that is the appropriate length (e.g., in seconds) and that has an appropriate number of samples.

At 510, process 500 can receive an output from the CNN that is indicative of compensatory reserve or a likelihood of hemodynamic decompensation. For example, in some embodiments, the output of the CNN can be a CRM value that is an estimate of the compensatory reserve of the subject from which the data was gathered.

At 512, process 500 can cause information indicative of a likelihood of decompensation to be presented. In some embodiments, the information can be presented using any suitable format and/or formats, and can be presented using any suitable presentation device. For example, in some embodiments, process 500 can cause the information to be presented visually in a numeric and/or graphical format. As another example, process 500 can cause the information to be presented using audio. As yet another example, process 500 can cause the information to be presented using tactile feedback.

FIG. 6 shows an example of a table of hyper parameter values that can be used to implement a convolutional neural network for estimating compensatory reserve and predicting hemodynamic decompensation using physiological data in accordance with some embodiments of the disclosed subject matter. Results described below in connection with FIG. 8 were generated using a CNN architecture based on the parameters shown in Table I of FIG. 6. The hyper parameter search space was modified according to the results generated by a first one thousand trial architectures, which were each trained for 100 epochs and evaluated using mongodb for parallel execution on a Cray Urika GX supercomputer. Based on the results generated by the first one thousand architectures, an additional two thousand candidate architectures were trained and evaluated. From those evaluations, the 120 architectures with the best validation scores were analyzed to select the best overall hyper parameters.

Figure 7:
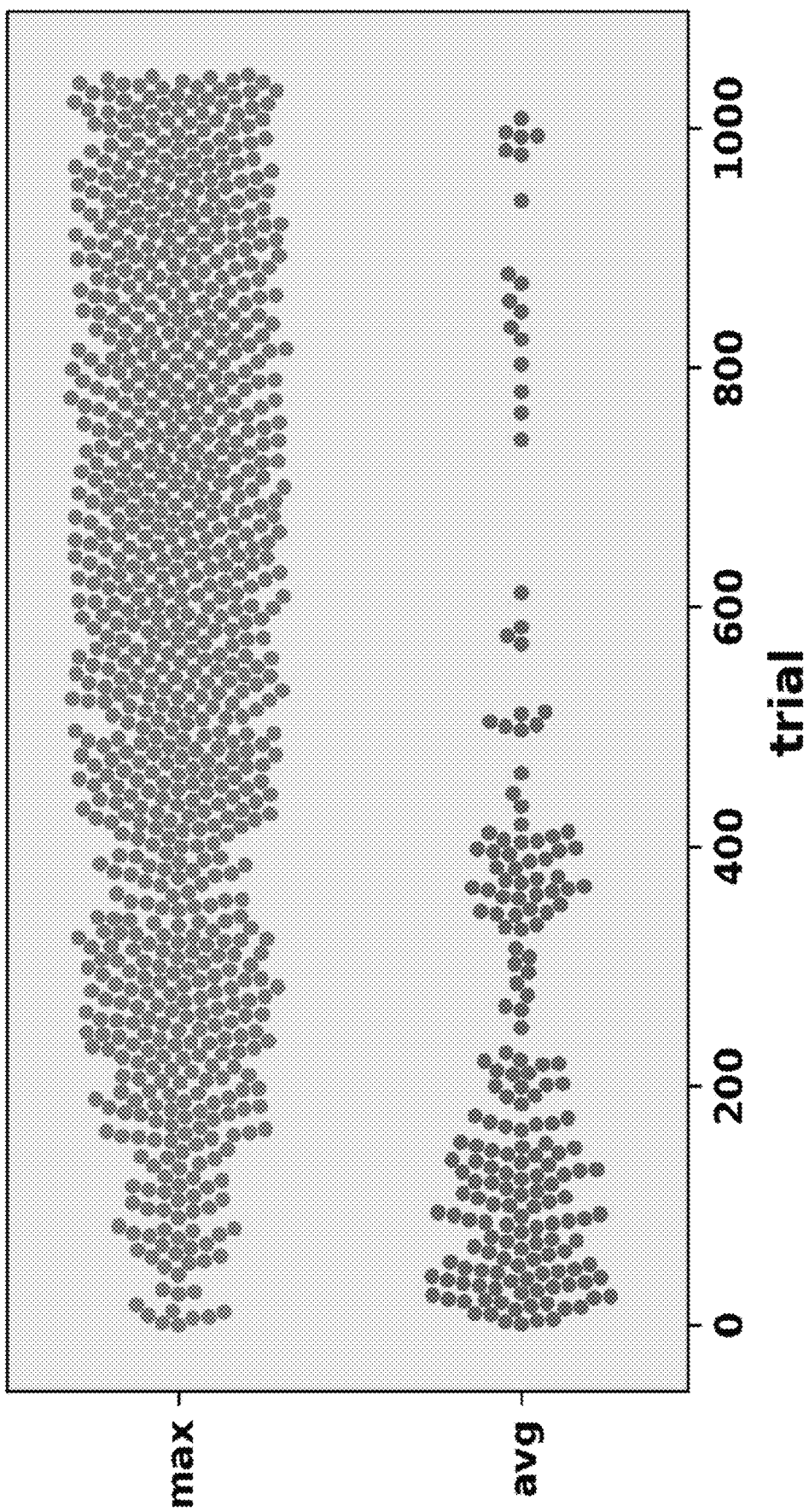
FIG. 7 shows an example of pooling types in various iterations of a convolutional neural network for estimating compensatory reserve and predicting hemodynamic decompensation using physiological data in accordance with some embodiments of the disclosed subject matter.

FIG. 7 shows an example of pooling types in various iterations of a convolutional neural network for estimating compensatory reserve and predicting hemodynamic decompensation using physiological data in accordance with some embodiments of the disclosed subject matter. From the results described in FIG. 6, it was inferred that several parameters should be fixed, and not subject to further optimization. For example, the swarm plot in FIG. 7 has one point per trial, grouped by pooling type, and shows that the optimizer developed a preference for max pooling over average pooling. This preference was validated by examining the training loss scores grouped by pooling type. The results were used to infer that using batch normalization, the 'Nadam' optimizer, and the Rectified Linear Unit (relu) as the activation function generated superior results.

Figure 8:
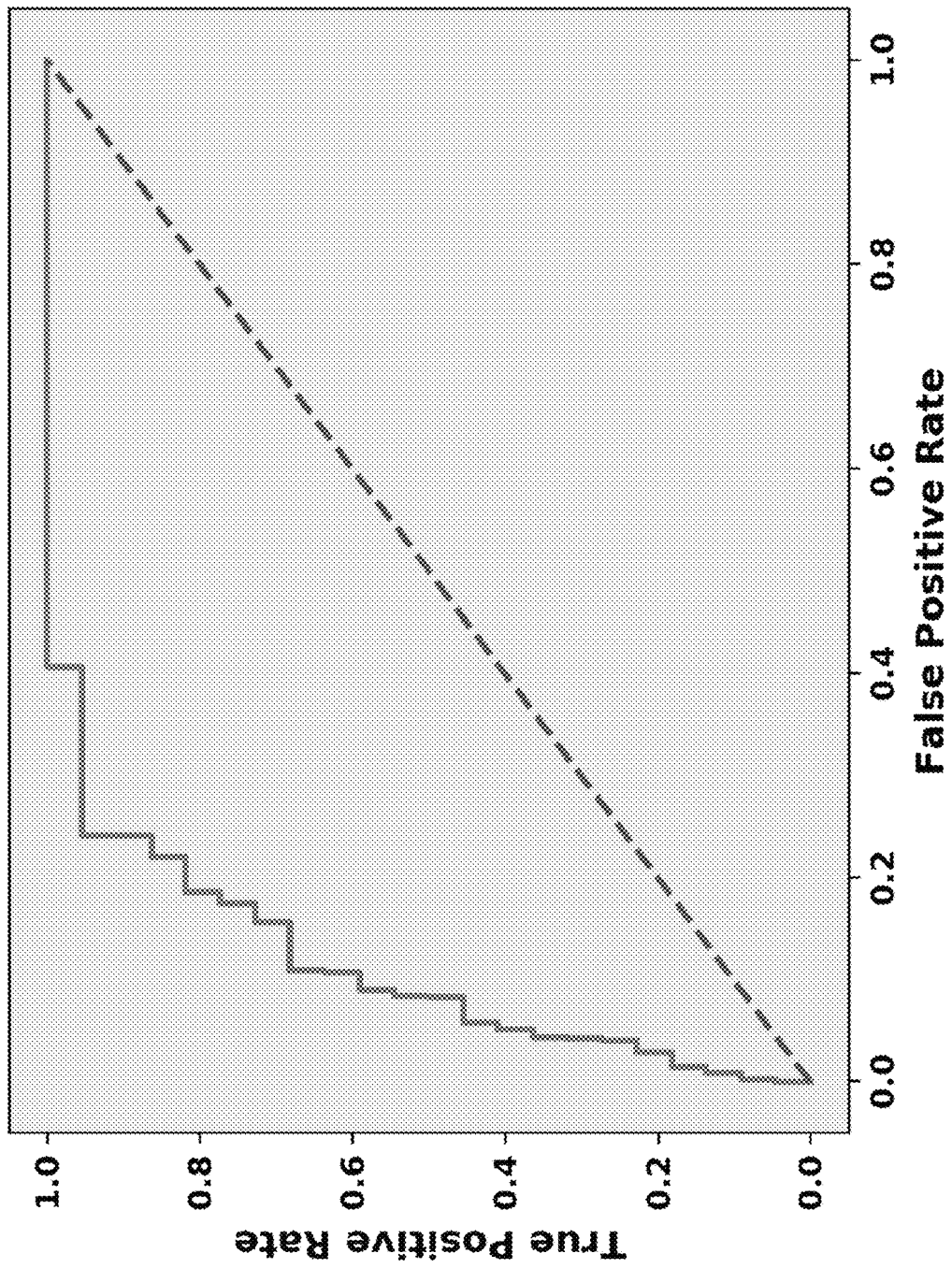
FIG. 8 shows an example of a Receiver Operating Characteristic Curve of a convolutional neural network for estimating compensatory reserve and predicting hemodynamic decompensation using physiological data implemented in accordance with some embodiments of the disclosed subject matter.

FIG. 8 shows an example of a Receiver Operating Characteristic Curve of a convolutional neural network for estimating compensatory reserve and predicting hemodynamic decompensation using physiological data implemented in accordance with some embodiments of the disclosed subject matter. The results shown in FIG. 8 were generated using data associated with 216 subjects with complete photoplethysmography blood pressure waveform recordings. Although no demographic information was available, the LBNP experimental results indicate that the subjects were a mixture of high tolerance and low tolerance individuals, where low tolerant individuals failed to complete the LBNP protocol through −60 mmHg and high tolerant individuals did complete this step. The results indicate that training a CNN using a mixture of data from low tolerance and high tolerance individuals allows the CNN to automatically account for high and low tolerance by predicting CRM as a percentage of the subject's individual tolerance.

The results shown in FIG. 8 were generated by a CNN with an architecture constructed using Python and the Keras library. The CNN was trained on the entire training set of 194 subjects and 30,075 waveform samples for 200 epochs to produce a CRM model with mean squared error (MSE) of 0.0236 and an R-squared (R2) score of 0.8670. The CRM model was used to generate results using waveforms extracted from the test data set corresponding to 22 subjects and 3,290 waveform samples to produce CRM scores for those LBNP experiments. The predictions were compared to the target CRM scores for the test subjects, yielding an overall MSE of 0.0238 and R2 score of 0.8903. The Generalized Estimating Equation method (GEE) was applied to produce a Receiver Operating Characteristic (ROC) area under the curve (AUC) for the point of decompensation of 0.8910, as shown in FIG. 8.

Figure 9:
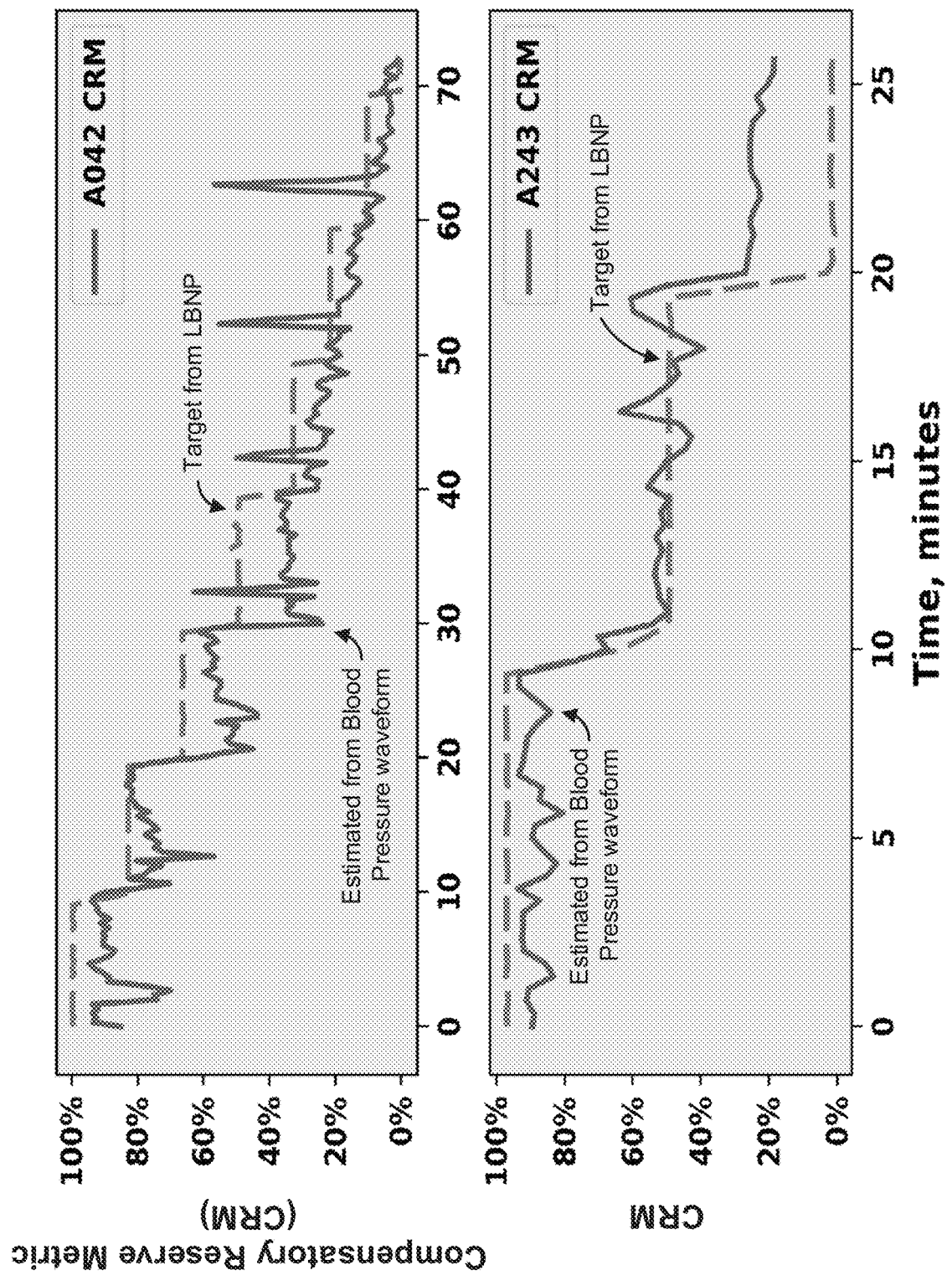
FIG. 9 shows examples of a compensatory reserve metric generated from samples of a blood pressure waveform in accordance with some embodiments of the disclosed subject matter and corresponding training targets calculated based on the labeled blood pressure waveform.
Figure 10:
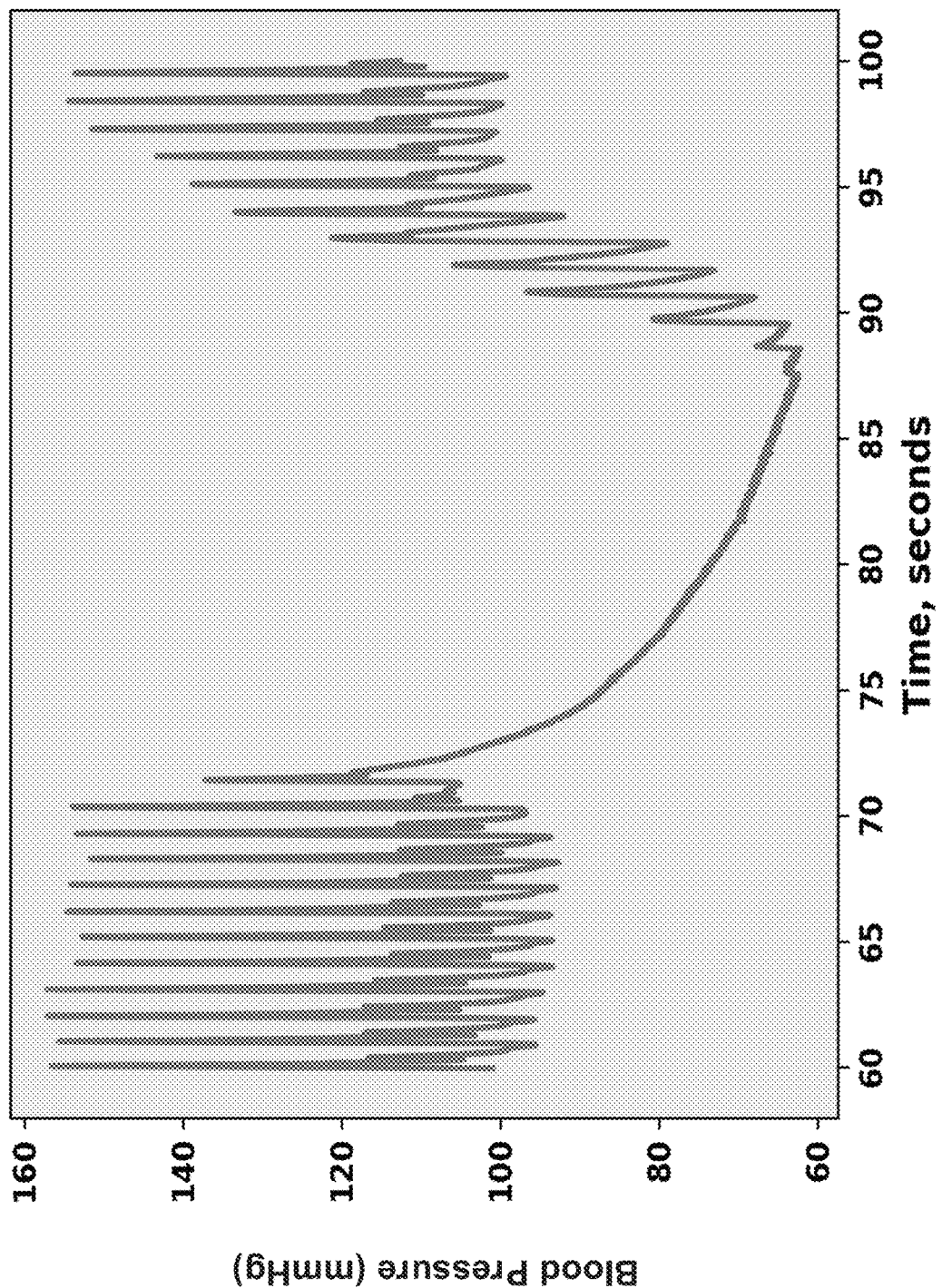
FIG. 10 shows an example of a blood pressure waveform that includes anomalous readings.

FIG. 9 shows examples of a compensatory reserve metric generated from samples of a blood pressure waveform in accordance with some embodiments of the disclosed subject matter and corresponding training targets calculated based on the labeled blood pressure waveform. The predicted CRM generated by the trained CNN described above in connection with FIG. 8 is shown compared to the stepped target CRM in FIG. 9 for two test subjects; one high tolerance and one low tolerance. In the examples shown in FIG. 9, the low tolerance individual is distinctly different in his/her time to decompensation, compared to the high tolerance individual (i.e., 25 vs 70 minutes, respectively). The predicted CRM closely matches the stepped target, as would be expected from the low error score shown in FIG. 8. The predicted CRM for the high tolerance subject (A042) shows several spikes, both positive and negative, shortly after changes in LBNP. These anomalies in the predicted CRM were not caused by instability of the CNN, but can instead be attributed to anomalies in the blood pressure waveform recordings, such as the anomaly shown in FIG. 10, recorded during the baseline recording phase of the LBNP experiment. It is not clear from the waveform data if the anomaly in FIG. 10 is a true reflection of the subject's physiology, or if it was an artifact of the instrumentation and data collection, but it is clear that the trained CNN can detect sudden changes in the blood pressure waveforms, whatever the cause.

Figure 11:
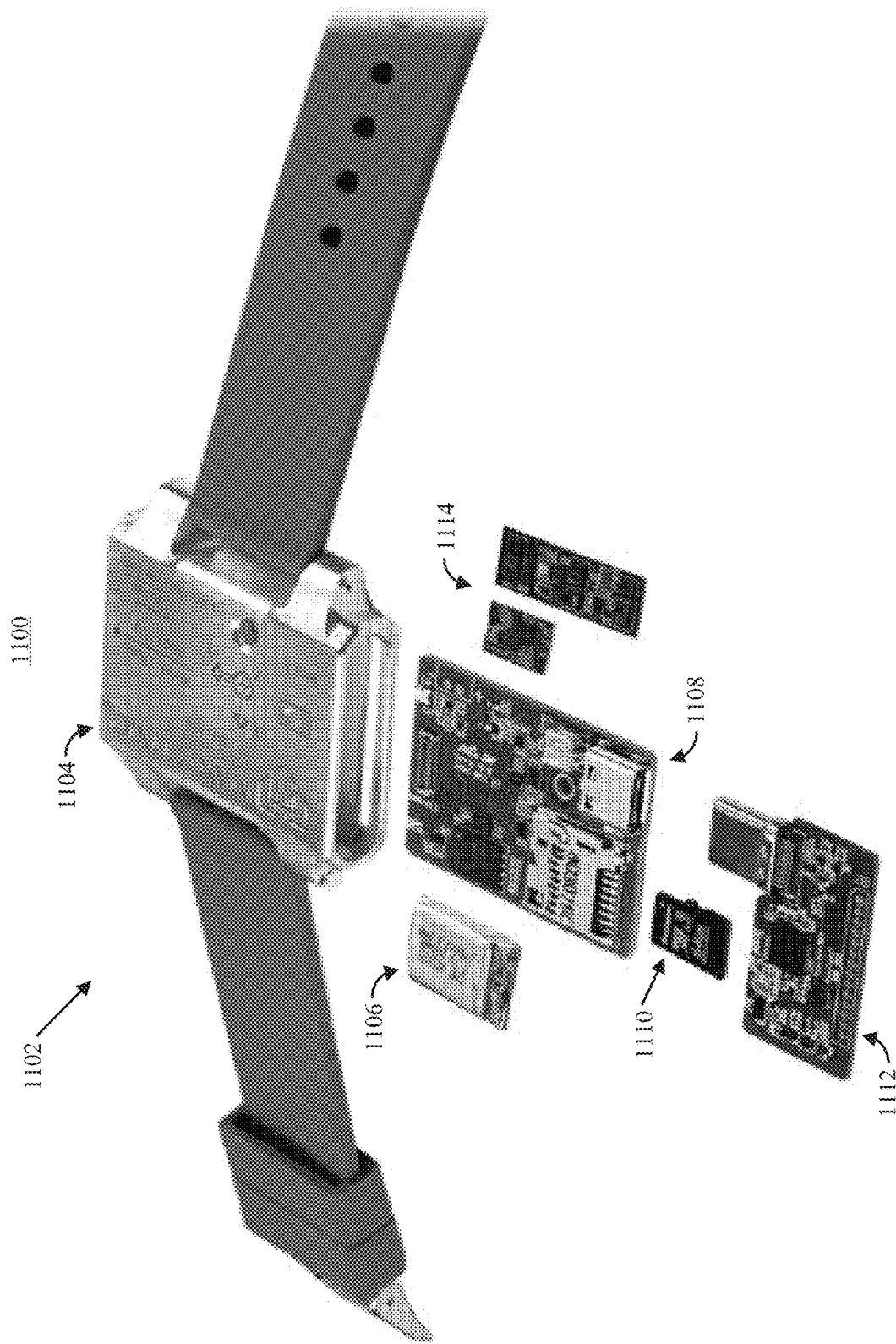
FIG. 11 shows an example of a compact device for recording physiological waveforms in accordance with some embodiments of the disclosed subject matter.

FIG. 11 shows an example 1100 of a compact device 1102 for recording physiological waveforms in accordance with some embodiments of the disclosed subject matter. In some embodiments, device 1102 can include an enclosure 1104 configured to be worn on the wrist, a rechargeable battery 1106, control electronics 1108, a non-volatile memory 1110, device auxiliary port sensors 1112, and sensor transducer board 1114.

In some embodiments, enclosure 1104 can be relatively compact. For example, the enclosure as shown in FIG. 11 has dimensions of about 35×35×12.6 mm$^3$ and a mass of about 19 grams. However, this is merely an example, and the enclosure can be configured to have different dimensions. Additionally, in some embodiments, enclosure 1104 be implemented using various form factors (e.g., form factors shown in FIG. 12).

In some embodiments, rechargeable battery 1106 can have any suitable capacity, which can provide a variable runtime based on the functions that device 1102 is configured to implement. For example, higher sampling rates and/or sampling multiple signals can cause the runtime to decrease as compared to sampling at lower rates and/or sampling a single signal.

In some embodiments, control electronics 1108 can include a circuit board and any suitable electronics for controlling operations of one or more components of device 1102 coupled to the circuit board. For example, control electronics 1108 can include one or more input/output interfaces configured to facilitate an interconnection with one or more other components, such as battery 1106, non-volatile memory 1110, device auxiliary port sensors 1112, and/or sensor transducer board 1114. For example, control electronics 1108 can control writing data to and/or reading data from non-volatile memory 1110. As another example, control electronics 1108 can receive data from device auxiliary port sensors 1112 and/or sensor transducer board 1114. In such an example, control electronics 1108 can analyze the received signal(s), and store the signal as received and/or the results of the analysis in non-volatile memory 1110.

In some embodiments, control electronics 1108 can include one or more processors that can be used to analyze data. In some embodiments, such a processor can be any suitable type or processor or combination of processors. For example, the processor can include one or more of a CPU, a GPU, an MCU, an ASIC, an FPGA, etc. As another example, control electronics 1108 can include control circuitry described below in connection with FIGS. 14 and 15.

In some embodiments, device auxiliary port sensors 1112 can include any suitable sensor and/or sensor interface. For example, device auxiliary port sensors 1112 can be used to expand the functionality of device 1102 by adding extra sensing capabilities.

In some embodiments, sensor transducer board 1114 can include any suitable communication circuitry to receive signals from and/or send signals to, one or more remote sensors.

In some embodiments, device auxiliary port sensors 1112 and/or sensor transducer board 1114 can be used to receive signals from one or more types of sensor, such as a HR signal obtained using an ECG sensor, an SpO2 signal obtained using a NIRS sensor, end tidal CO2 obtained using a capnography sensor, beat-to-beat systolic (SBP) and/or diastolic (DBP) blood pressure using a photoplethysmography sensor, etc.

In some embodiments, device 1102 can be used to simultaneously capture, in real-time, several waveforms such as multi-lead ECG signals, and photoplethysmography signals. In some embodiments device 1102 can be configure to acquire the data at a rate that is programmable up to 1,500 samples per second per waveform providing high quality data for analysis. For example, device 1102 can be configured to receive signals from standard clinical ECG leads (e.g., RE product number 490, 5-lead ECG Snap Set with 36 inch leads) and patches (e.g., 3M model 2570). As another example, device 1102 can be configured to receive signals from standard clinical photoplethysmography sensors (e.g., Masimo LNCS TF-1 SpO2 reusable forehead sensor), which is sometimes referred to as a pulse oximeter. As yet another example, device 1102 can be implemented as an autonomous ambulatory monitoring, that has a relatively unobtrusive form factor (e.g., 35×35×12.6 mm$^3$ and 19 grams) with a runtime of eight hours when collecting waveforms at the highest data sample rate setting (e.g., 1,500 samples per second). In such an example, data can be stored on-device and/or sent to a remote storage device for offline analysis.

In some embodiments, device 1102 can be implemented to perform one or more functions of computing device 110 described above in connection with FIGS. 1 and 2. For example, in some embodiments, device 1102 can be implemented to execute one or more portions of compensatory reserve estimation system. Additionally or alternatively, in some embodiments, device 1102 can be implemented to perform one or more functions of physiological data source 102 described above in connection with FIG. 1. For example, in some embodiments, device 1102 can output data (e.g., samples, waveforms based on the samples, metrics, etc.) to another device (e.g., a computing device 110, server 120), which can be used to provide one or more user interfaces for a user. In a more particular example, device 1102 can transmit (e.g., using a wired interface and/or wireless interface) data such as samples, waveforms based on the samples, and/or metrics to a computing device 110 and/or server 120, and computing device 110 and/or server 120 can provide access to the data via a user interface. In some embodiments, computing device 110 and/or server 120 can provide access to the data via an application being executed by computing device 110 and/or server 120. Additionally or alternatively, in some embodiments, computing device 110 and/or server 120 can generate an alert that is communicated to any suitable user using any suitable technique. For example, in some embodiments, computing device 110 and/or server 120 can generate an alert when a subject's compensatory reserve falls below a particular threshold. As another example, computing device 110 and/or server 120 can cause an alert to be provided (e.g., to a user of computing device 110 and/or server 120) who may or may not be the subject being monitored using device 1102. In a more particular example, a user can be the subject being monitored using device 1102. As another more particular example, a user can be a healthcare provider associated with the subject being monitored. As yet another more particular example, a user can be a provider of emergency services (e.g., a public emergency service such as 911, or a private emergency service provider). In such examples, the alert can be provided as a notification (e.g., a push notification) via a computing device 110 associated with the user, via a phone number associated with the user (e.g., as a text message, or audio message), via an email address associated with the user, and/or using any other suitable technique or combination of techniques.

Figure 12:
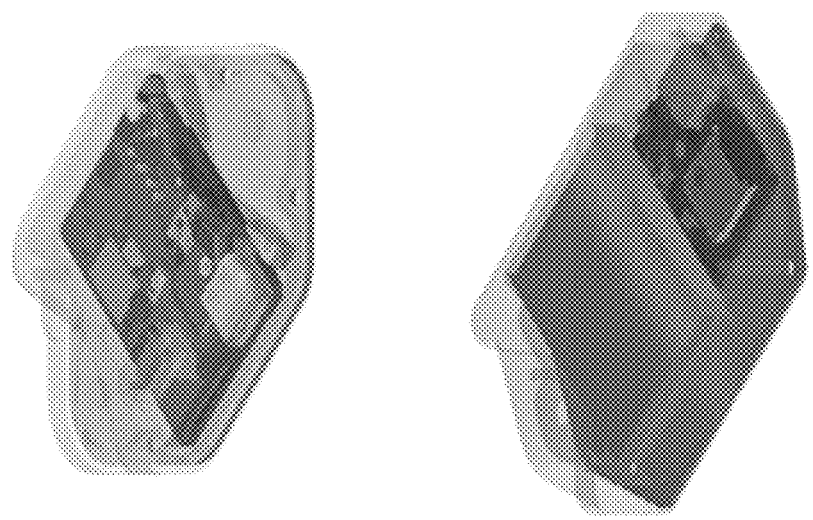
FIG. 12 shows examples of enclosures that can be used to house components of a compact device that for recording physiological waveforms in accordance with some embodiments of the disclosed subject matter.
Figure 12:
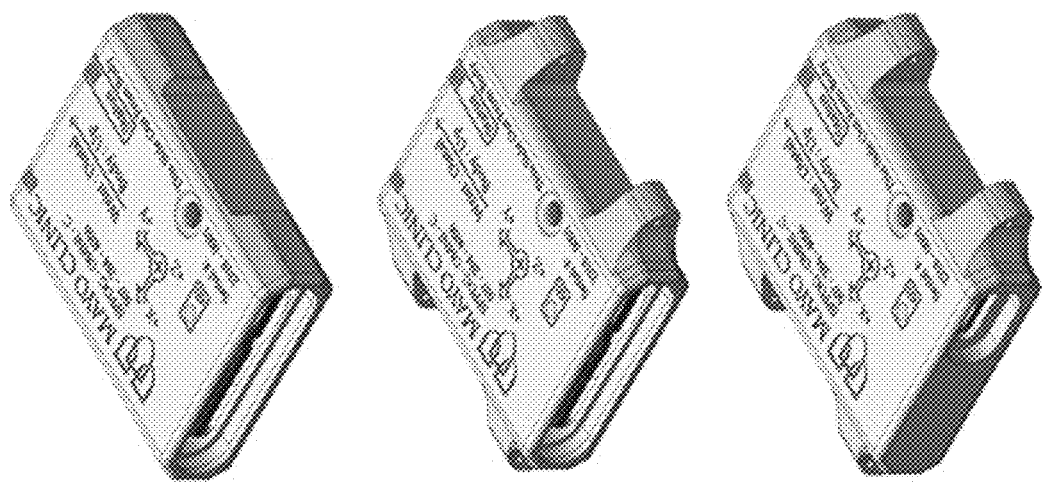

FIG. 12 shows examples of enclosures that can be used to house components of a compact device that for recording physiological waveforms in accordance with some embodiments of the disclosed subject matter.

Figure 13:
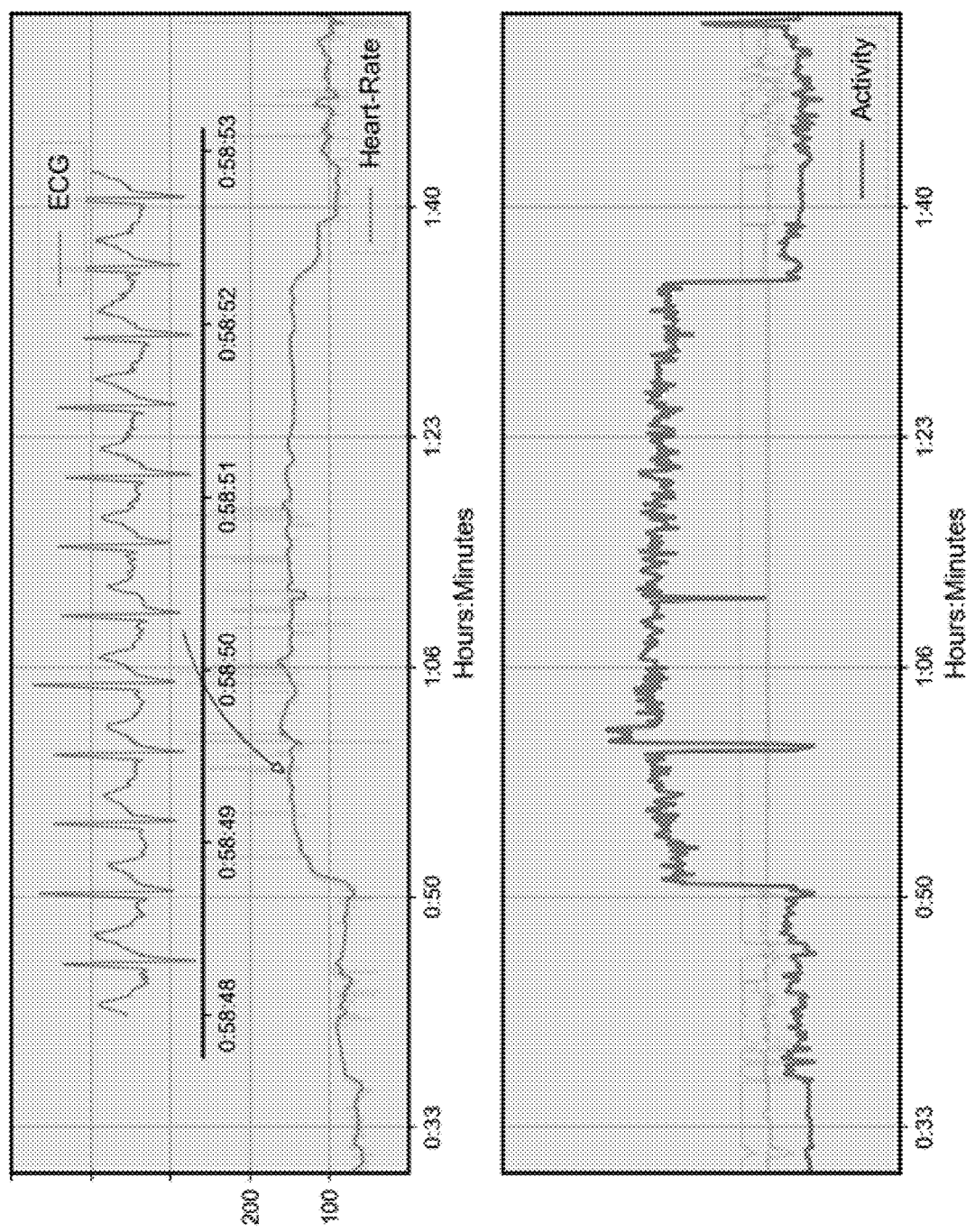
FIG. 13 shows an example of information recorded and generated by a compact device for recording physiological waveforms implemented in accordance with some embodiments of the disclosed subject matter.

FIG. 13 shows an example of information recorded and generated by a compact device for recording physiological waveforms implemented in accordance with some embodiments of the disclosed subject matter. As shown in FIG. 13, device 1102 can record an ECG signal, which can be analyzed by device 1102 to generate a heart rate waveform. Additionally, in some embodiments, device 1102 can generate an "activity" metric based on the heart rate waveform.

Figure 14:
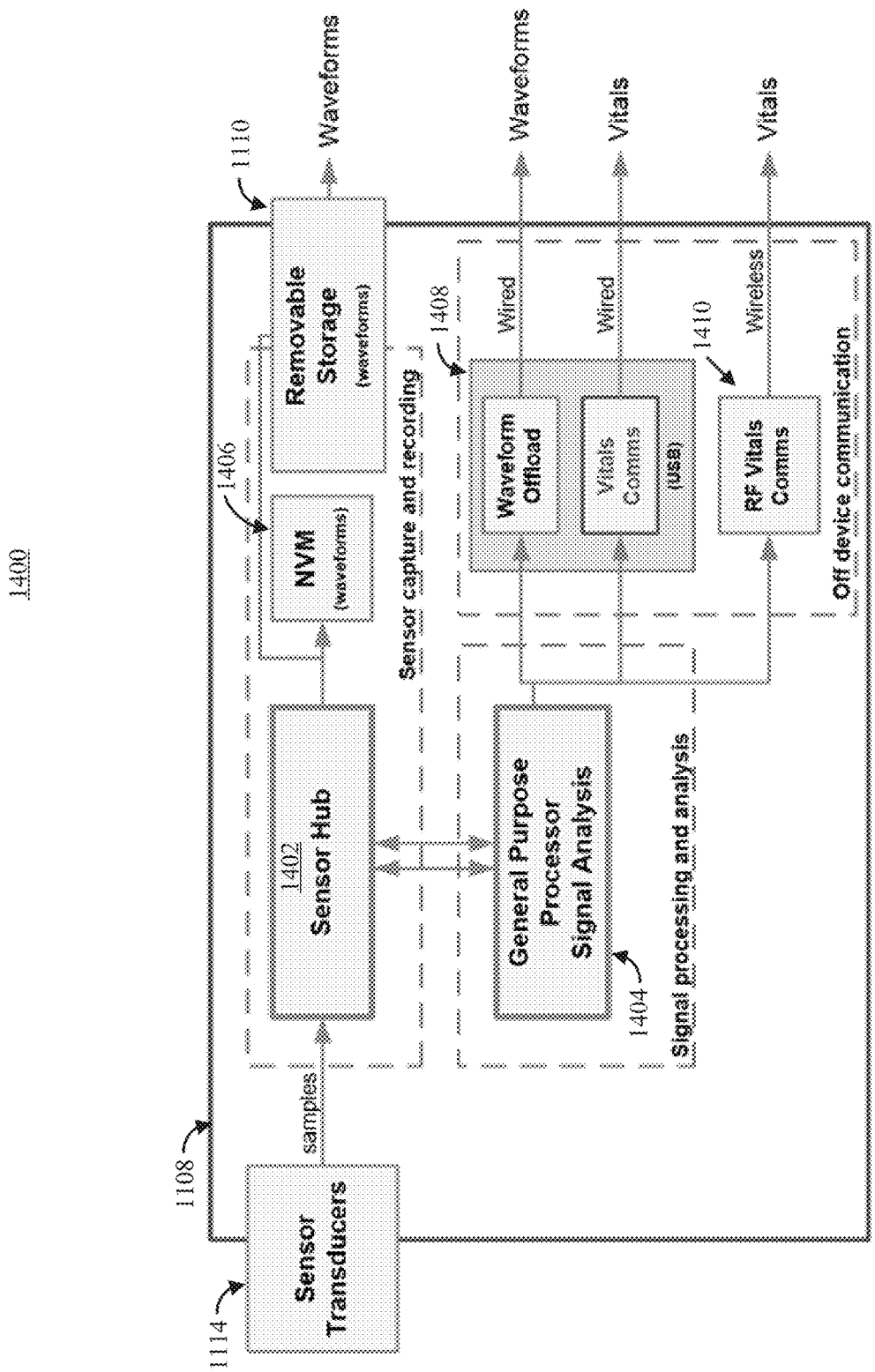
FIG. 14 shows an example of hardware components that can be used to implement a compact device for recording physiological waveforms implemented in accordance with some embodiments of the disclosed subject matter.

FIG. 14 shows an example 1400 of hardware components that can be used to implement a compact device for recording physiological waveforms implemented in accordance with some embodiments of the disclosed subject matter. In some embodiments, the components shown in FIG. 14 can be used in an implementation of device 1102.

In some embodiments, hardware 1400 can include control electronics 1108, a removable non-volatile memory 1110, and sensor transducers 1114 which can be in communication with one or more sensors. In some embodiments, control electronics 1108 can include a sensor hub 1402 that can receive signals from one or more sensors (e.g., as sampled by sensor transducers 1114) and can provide the signals to general purpose processor 1404 for analysis and/or transmission to another device. In some embodiments, sensor hub 1402 can store raw data in an internal non-volatile memory 1406 and/or removable non-volatile memory 1110.

In some embodiments, general purpose processor 1404 can perform one or more analyses using the data and/or can encode the data for transmission to another device. For general purpose processor 1404 can encode waveforms for transmission over a wired interface (e.g., a USB interface) and/or a wireless interface (e.g., Bluetooth, Wi-fi, cellular, etc.). In some embodiments, general purpose processor 1404 can generate one or more signals and/or metrics based on the data received from sensor hub 1402 such as vital information such as heart rate or CRM that is derived from the signals received from the sensors.

In some embodiments, hardware 1400 can include a wired interface 1408 and/or a wireless interface 1410, which can be used to output waveforms and/or information derived from such waveforms. In some embodiments, wired interface 1408 and/or a wireless interface 1410 can implement at least a portion of communication systems 208 described above in connection with FIG. 2 and/or can be implemented using one or more components described above in connection with communication systems 208. For example, in some embodiments, wireless interface 1410 can include one or more transmitters, receivers, and/or transceivers.

Figure 15:
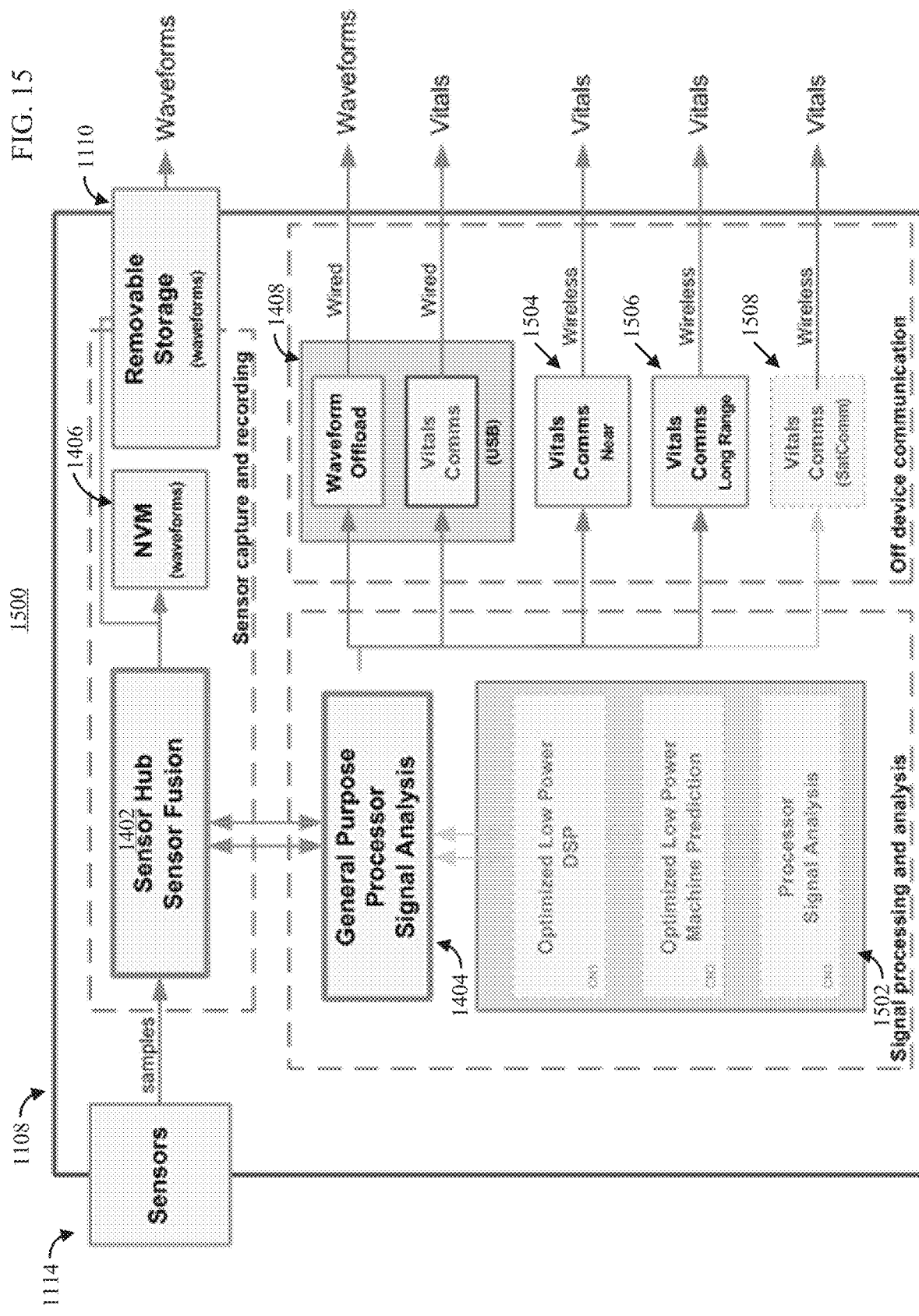
FIG. 15 shows an example of hardware components that can be used to implement a scalable compact device for recording physiological waveforms implemented in accordance with some embodiments of the disclosed subject matter.

FIG. 15 shows an example 1500 of hardware components that can be used to implement a scalable compact device for recording physiological waveforms implemented in accordance with some embodiments of the disclosed subject matter. In some embodiments, the components shown in FIG. 15 can be used in an implementation of device 1102.

In some embodiments, hardware 1500 can include many similar components to hardware 1400, and can additionally include one or more special purpose processors 1502, and additional communications hardware components such as short range wireless communication components 1504 (e.g., Bluetooth, Wi-Fi), long range wireless communication components 1506 (e.g., cellular communications), and/or satellite communication components 1508. In some embodiments, short range wireless communication components 1504, long range wireless communication components 1506, and/or satellite communication components 1508 can implement at least a portion of communication systems 208 described above in connection with FIG. 2 and/or can be implemented using one or more components described above in connection with communication systems 208. For example, in some embodiments, short range wireless communication components 1504, long range wireless communication components 1506, and/or satellite communication components 1508 can include one or more transmitters, receivers, and/or transceivers.

In some embodiments, special purpose processors 1502 can be implemented as ASICs and/or FPGAs. In some embodiments, each special purpose process can perform one or more particular tasks. For example, a special purpose processor can be implemented to execute one or more portions of compensatory reserve estimation system 104.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

It should be understood that the above described steps of the processes of FIG. 5 can be executed or performed in any order or sequence not limited to the order and sequence shown and described in the figures. Also, some of the above steps of the processes of FIG. 5 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A system for estimating compensatory reserve, the system comprising:
at least one hardware processor that is programmed to:
receive a blood pressure waveform of a subject;
generate a first sample of the blood pressure waveform, wherein the first sample comprises a time series of blood pressure values having a first duration;
provide the first sample as input to a trained one-dimensional (1D) convolutional neural network (CNN),
wherein the 1D CNN was trained as a regression model using samples of the first duration from blood pressure waveforms recorded from a plurality of subjects while decreasing the respective subject's central blood volume,
wherein each sample used to train the 1D CNN is a one-dimensional time series data structure that was associated with a compensatory reserve metric based on a decrease of the respective subject's central blood volume at a time the respective sample was recorded, and
wherein an output layer of the trained 1D CNN is a linear layer that outputs a compensatory reserve metric value;
receive, from the trained 1D CNN, a first compensatory reserve metric based on the first sample, wherein the first compensatory reserve metric is a single quantitative value indicating a percentage of compensatory reserve in the subject; and
cause information indicative of remaining compensatory reserve to be presented.

2. The system of claim 1, wherein the first duration is in a range of 2 seconds to 30 seconds.

3. The system of claim 2, wherein the first duration is 20 seconds.

4. The system of claim 1, wherein the 1D CNN comprises a convolutional layer group, one or more fully connected layers following the convolutional layer group, and the output layer, wherein the output layer is configured to compute the compensatory reserve metric based on values received from a fully connected layer of the one of more fully connected layers.

5. The system of claim 1, wherein the blood pressure waveforms recorded from the plurality of subjects were recorded while varying amounts of negative pressure were applied to each subject's lower body.

6. A method for estimating compensatory reserve, the method comprising:
receiving a blood pressure waveform of a subject;
generating a first sample of the blood pressure waveform, wherein the first sample comprises a time series of blood pressure values having a first duration;
providing the first sample as input to a trained one-dimensional (1D) convolutional neural network (CNN),
wherein the 1D CNN was trained as a regression model using samples of the first duration from blood pressure waveforms recorded from a plurality of subjects while decreasing the respective subject's central blood volume,
wherein each sample used to train the 1D CNN is a one-dimensional time series data structure that was associated with a compensatory reserve metric based on a decrease of the respective subject's central blood volume at a time the respective sample was recorded, and
wherein an output layer of the trained 1D CNN is a linear layer that outputs a compensatory reserve metric value;
receiving, from the trained 1D CNN, a first compensatory reserve metric based on the first sample, wherein the first compensatory reserve metric is a single quantitative value indicating a percentage of compensatory reserve in the subject; and
causing information indicative of remaining compensatory reserve to be presented.

7. The method of claim 6, wherein the first duration is in a range of 2 seconds to 30 seconds.

8. The method of claim 7, wherein the first duration is 20 seconds.

9. The method of claim 6, wherein the 1D CNN comprises a convolutional layer group, one or more fully connected layers following the convolutional layer group, and the output layer, wherein the output layer is configured to compute the compensatory reserve metric based on values received from a fully connected layer of the one of more fully connected layers.

10. The method of claim 6, wherein the blood pressure waveforms recorded from the plurality of subjects were recorded while varying amounts of negative pressure were applied to each subject's lower body.

11. The system of claim 1, wherein the first compensatory reserve metric predicts the subject's progress toward hemodynamic decompensation with respect to a predicted baseline of the subject based on the blood pressure waveform.

12. The system of claim 1, wherein the plurality of subjects includes a subset of low tolerant subjects that experienced hemodynamic compensation at a lower body negative pressure (LBNP) of less than 60 millimeters of mercury (mmHg), and a subset of high tolerant subjects that experienced hemodynamic compensation at an LBNP of more than 60 mmHg.

13. The method of claim 6, wherein the first compensatory reserve metric is indicative of the subject's progress to hemodynamic decompensation with respect to a predicted baseline of the subject based on the blood pressure waveform.

14. The method of claim 6, wherein the plurality of subjects includes a subset of low tolerant subjects that experienced hemodynamic compensation at a lower body negative pressure (LBNP) of less than 60 millimeters of mercury (mmHg), and a subset of high tolerant subjects that experienced hemodynamic compensation at an LBNP of more than 60 mmHg.

* * * * *